United States Patent [19]

Weinshank et al.

[11] Patent Number: 5,476,782
[45] Date of Patent: Dec. 19, 1995

[54] DNA ENCODING A HUMAN 5-HT$_{1E}$ RECEPTOR AND USES THEREOF

[75] Inventors: Richard L. Weinshank, New York, N.Y.; Theresa Branchek, Teaneck; Paul R. Hartig, Mahwah, both of N.J.

[73] Assignee: Synaptic Pharmaceutical Corporation, Paramus, N.J.

[21] Appl. No.: 370,542

[22] Filed: Jan. 9, 1995

Related U.S. Application Data

[63] Continuation of Ser. No. 194,113, Feb. 8, 1994, abandoned, which is a continuation of Ser. No. 803,626, Dec. 2, 1991, abandoned.

[51] Int. Cl.$^6$ ............ C07H 21/04; C12N 5/10; C12N 15/12
[52] U.S. Cl. ............ 435/240.2; 536/23.5; 435/172.1; 530/350; 935/9
[58] Field of Search ............ 435/172.1, 240.2, 435/69.1, 70.3, 71.1, 71.2, 320.1, 252.3, 254.11; 514/12, 21; 536/23.5; 530/350

[56] References Cited

U.S. PATENT DOCUMENTS

| | | | |
|---|---|---|---|
| 4,675,285 | 6/1987 | Clark | 435/6 |
| 4,904,582 | 2/1990 | Tullis | 435/6 |
| 4,985,352 | 1/1991 | Julius et al. | 435/6 |
| 5,155,218 | 10/1992 | Weinshank et al. | 536/27 |
| 5,360,735 | 11/1994 | Weinshank et al. | 435/240.2 |

OTHER PUBLICATIONS

N. Adnam et al. PNAS 90(2):408–412 Jan. 15, 1993.
F. J. Monsma et al. Molecular Pharmacology 43(3):320 Mar. 1993.
Izant et al. Cell 36:1007–1015, 1984 Inhibition of TK Gene Expr by Anti Sense RNA.
Masu et al Nature 329:836–838 Oct. 29, 1987 cDNA cloning of bovine substance K receptor.
Leonhardt et al. J. Neurochem 53(2)465–471 1989.
Julius, D. et al. Science 241:558–560 Jul. 29, 1988.
Nichols, Eve K. Human Gene Therapy. National Academy of Sciences, 1988 p. 118.
E. Uhlmann et al Chem Rev 90(4)544–584 1990.

*Primary Examiner*—Marianne P. Allen
*Assistant Examiner*—Lorraine M. Spector
*Attorney, Agent, or Firm*—John P. White

[57] ABSTRACT

This invention provides an isolated nucleic acid molecule encoding a human 5-HT$_{1E}$ receptor, an isolated protein which is a human 5-HT$_{1E}$ receptor, vectors comprising an isolated nucleic acid molecule encoding a human 5-HT$_{1E}$ receptors, mammalian cells comprising such vectors, antibodies directed to the human 5-HT$_{1E}$ receptor, nucleic acid probes useful for detecting nucleic acid encoding human 5-H$_{1E}$ receptors, antisense oligonucleotides complementary to any sequences of a nucleic acid molecule which encodes a human 5-HT$_{1E}$ receptor, pharmaceutical compounds related to human 5-HT$_{1E}$ receptors, and nonhuman transgenic animals which express DNA a normal or a mutant human 5-HT$_{1E}$ receptor. This invention further provides methods for determining ligand binding, detecting expression, drug screening, and treatment involving the human 5-HT$_{1E}$ receptor.

13 Claims, 9 Drawing Sheets

FIGURE 1A

| FIGURE 1A |
|-----------|
| FIGURE 1B |
| FIGURE 1C |
| FIGURE 1D |

```
        -730              -710              -690
ATATACATCATGGAATACTATGCAGCCCCCCCCAAGGATGCGTTCCATGTCCTTTGCAGG
        -670              -650              -630
GACATGGATGAGTTGCAAACCATATTCTCAACAAACTAACACAGCCACAGAAAACCAAAC
        -610              -590              -570
ACCACATGCTCTCACTCACGAGTGGAGTTGAACAATGAGAACACATGGCACAGGGCCGGG
        -550              -530              -510
AACATGACACACCAGGGCCTGTTGGGGGGTGGAGGGCTAGGGGAGGGATGGCATTAGGAG
        -490              -470              -450
AAGTACCTAATGTAGATGATTGGTTGTTGGGTGCAGCAAACCACCATGGCACATGTATAC
        -430              -410              -390
CTATGTAGCAAACCTGCAAGTTCTGCACATGTATCCCAGGACTTAAAGTATAATTTAAAA
        -370              -350              -330
AAAAACAGTTTGAAAACTTCCCTGAAGTAAAAAAAGTATCCTTTGAGGAACAATGTAACG
        -310              -290              -270
ATGAGCTCAAGTTCCACAGGAAAGAGAAAATTAAAATTTATAAAGAATTTATAAATATCA
        -250              -230              -210
AACTATTTCATGTTTTCCAGGAAAAGTGTGGCTTTCTCATTCATTAACCAATAGCATAA
        -190              -170              -150
TATTTTCCAGGAACCTTCACTCAGAAGAAATGCTGTGGCCCTTCCCTTTACCAACAGAAA
        -130              -110              -90
ATGGAACACAAGAGACCACATAGCTGAACAAATTATAGCCTCCTTACAAGTGAGAAACCT
        -70               -50               -30
TCGAGGCTACATAGTTTTCAGCCAAAGGAAAATAACCAACAGCTTCTCCACAGTGTAGAC
        -10                10                30
```

FIGURE 1B

```
TGAAACAAGGGAAACATGAACATCACAAACTGTACCACAGAGGCCAGCATGGCTATAAGA
                  M   N   I   T   N   C   T   T   E   A   S   M   A   I   R
     50                     70                      90

CCCAAGACCATCACTGAGAAGATGCTCATTTGCATGACTCTGGTGGTCATCACCACCCTC
 P   K   T   I   T   E   K   M   L   I   C   M   T   L   V   V   I   T   T   L
     110                    130                     150

ACCACGTTGCTGAACTTGGCTGTGATCATGGCTATTGGCACCACCAAGAAGCTCCACCAG
 T   T   L   L   N   L   A   V   I   M   A   I   G   T   T   K   K   L   H   Q
     170                    190                     210

CCTGCCAACTACCTAATCTGTTCTCTGGCCGTGACGGACCTCCTGGTGGCAGTGCTCGTC
 P   A   N   Y   L   I   C   S   L   A   V   T   D   L   L   V   A   V   L   V
     230                    250                     270

ATGCCCCTGAGCATCATCTACATTGTCATGGATCGCTGGAAGCTTGGGTACTTCCTCTGT
 M   P   L   S   I   I   Y   I   V   M   D   R   W   K   L   G   Y   F   L   C
     290                    310                     330

GAGGTGTGGCTGAGTGTGGACATGACCTGCTGCACCTGCTCCATCCTCCACCTCTGTGTC
 E   V   W   L   S   V   D   M   T   C   C   T   C   S   I   L   H   L   C   V
     350                    370                     390

ATTGCCCTGGACAGGTACTGGGCCATCACCAATGCTATTGAATACGCCAGGAAGAGGACG
 I   A   L   D   R   Y   W   A   I   T   N   A   I   E   Y   A   R   K   R   T
     410                    430                     450

GCCAAGAGGGCCGCGCTGATGATCCTTACCGTCTGGACCATCTCCATTTTCATCTCCATG
 A   K   R   A   A   L   M   I   L   T   V   W   T   I   S   I   F   I   S   M
     470                    490                     510

CCCCCTCTGTTCTGGAGAAGCCACCGCCGCCTAAGCCCTCCCCCTAGTCAGTGCACCATC
 P   P   L   F   W   R   S   H   R   R   L   S   P   P   P   S   Q   C   T   I
     530                    550                        570
```

FIGURE 1C

```
CAGCACGACCATGTTATCTACACCATTTACTCCACGCTGGGTGCGTTTTATATCCCCTTG
 Q   H   D   H   V   I   Y   T   I   Y   S   T   L   G   A   F   Y   I   P   L
    590                 610                 630
ACTTTGATACTGATTCTCTATTACCGGATTTACCACGCGGCCAAGAGCCTTTACCAGAAA
 T   L   I   L   I   L   Y   Y   R   I   Y   H   A   A   K   S   L   Y   Q   K
    650                 670                 690
AGGGGATCAAGTCGGCACTTAAGCAACAGAAGCACAGATAGCCAGAATTCTTTTGCAAGT
 R   G   S   S   R   H   L   S   N   R   S   T   D   S   Q   N   S   F   A   S
    710                 730                 750
TGTAAACTTACACAGACTTTCTGTGTGTCTGACTTCTCCACCTCAGACCCTACCACAGAG
 C   K   L   T   Q   T   F   C   V   S   D   F   S   T   S   D   P   T   T   E
    770                 790                 810
TTTGAAAAGTTCCATGCCTCCATCAGGATCCCCCCCTTCGACAATGATCTAGATCACCCA
 F   E   K   F   H   A   S   I   R   I   P   P   F   D   N   D   L   D   H   P
    830                 850                 870
GGAGAACGTCAGCAGATCTCTAGCACCAGGGAACGGAAGGCAGCACGCATCCTGGGGCTG
 G   E   R   Q   Q   I   S   S   T   R   E   R   K   A   A   R   I   L   G   L
    890                 910                 930
ATTCTGGGTGCATTCATTTTATCCTGGCTGCCATTTTTCATCAAAGAGTTGATTGTGGGT
 I   L   G   A   F   I   L   S   W   L   P   F   F   I   K   E   L   I   V   G
    950                 970                 990
CTGAGCATCTACACCGTGTCCTCGGAAGTGGCCGACTTTCTGACGTGGCTCGGTTATGTG
 L   S   I   Y   T   V   S   S   E   V   A   D   F   L   T   W   L   G   Y   V
   1010                1030                1050
AATTCTCTGATCAACCCTCTGCTCTATACGAGTTTTAATGAAGACTTTAAGCTGGCTTTT
 N   S   L   I   N   P   L   L   Y   T   S   F   N   E   D   F   K   L   A   F
```

FIGURE 1D

```
     1070                    1090                   1110
AAAAAGCTCATTAGATGCCGAGAGCATACTTAGACTGTAAAAAGCTAAAAGGCACGACTT
 K   K   L   I   R   C   R   E   H   T
     1130                    1150                   1170
TTTCCAGAGCCTCATGAGTGGATGGGGGTAAGGGGTGCAACTTATTAATTCTTGAACATA
     1190                    1210                   1230
CTTGGTTCAGGAGAGTTTGTAAGTATGTGTGGTCTTGTTTCCTTGTTTGTTTGTTTGTTT
     1250                    1270                   1290
TGTTCTGTTTTGTTTGAGGATTGTTATTTGGCCTCCTGTTTTCTACCTCTGGTCTTATCT
     1310                    1330                   1350
GTGATACATAATTTCAAATAAACATTATCATACAAAAACAGAAATTTTGCCAGAAGTAAT
     1370                    1390                   1410
AATAAGATGAAATACTAAATACCTTTTATGGGTTTTTTTTTTTAGCCATTTCAGTTACC
     1430                    1450                   1470
CTGCAATTAAAGAATGCCAAAAATATCTTTATTTGCAGAATTTCTTATTACTTATAAATT
     1490                    1510                   1530
AAATACCTGATAATGCCCTCCATGGCATTAAATCTGAGATTATGGCTCTATCTGCGTACA
     1550                    1570                   1590
TATTCCAGTGGGAATTGCATGACTACATAAAGAATTAAAAGAAAGTGATGTGCTGTCATC
     1610                    1630                   1650
TACGGCTTGCGACCTGAGCTAAAGTCGGGGGCTGTAGCACTGTGACTACGTAGCCTATCA
     1670                    1690                   1710
TTTCAGGTAAAAATAGTACAGCTGGCTTGTCTTGTTAGTTCATGATTAAATAAACTTCTC

TTT
```

FIGURE 2A

| FIGURE 2A |
|-----------|
| FIGURE 2B |

```
                1                                                              50
    5HT1C       M..........  ..........  ...VNLGNAV  RSLLMHLIGL  LVWQFDISIS
    5HT2        MDILCEENTS   LSSTTNSLMQ  LNDDTRLYSN  DFNSGEANTS  DAFNWTVDSE
    5HT1Dα      M..........  ..........  ..........  ......SPLN  QSAEGLPQEA
    5HT1Dβ      M..........  ..........  ..........  ........EE  PGAQCAPPAP  AGSETWVPQA
    5HT1E       M..........  ..........  ..........  ..........  ..........
    5HT1A       M..........  ..........  ..........  ..........  .DVLSPGQGN
TM Region       ..........  ..........  ..........  ..........  ..........

51                                                             100
    5HT1C       PVAAIVTDTF   NSSDGGRLFQ  FPDGVQNWPA  LSIVVIIIMT  IGGNILVIMA
    5HT2        NRTNLSCEGC   LSPSCLSLLH  LQE..KNWSA  LLTAVVIILT  IAGNILVIMA
    5HT1Dα      ...SNRSLNA   TETSEAWDPR  TLQALKISLP  VLLSVITLAT  VLSNAFVLTT
    5HT1Dβ      NLSSAPSQNC   SAKDYIYQDS  ISLPWKVLLV  MLLALITLAT  TLSNAFVIAT
    5HT1E       .....NITNC   TTEASMAIRP  KTITEKMLIC  MTLVVITTLT  TLLNLAVIMA
    5HT1A       NTTSPPAPFE   TGGNTTGISD  VTVSYQVITS  LLLGTLIFCA  VLGNACVVAA
TM Region       ..........  ..........  .....*****  *******..   I..*******

101                                                            150
    5HT1C       VSMEKKLHNA   TNYFLMSLAI  ADMLVGLLVM  PLSLLAILYD  YVWPLPRYLC
    5HT2        VSLEKKLQNA   TNYFLMSLAI  ADMLLGFLVM  PVSMLTILYG  YRWPLPSKLC
    5HT1Dα      ILLTRKLHTP   ANYLIGSLAT  TDLLVSILVI  PISMAYTITH  .TWNFGQILC
    5HT1Dβ      VYRTRKLHTP   ANYLIASLDV  TDLLVSILVI  PISTMYTVTD  .RWTLSQVVC
    5HT1E       IGTTKKLHQP   ANYLICSLAV  TDLLVAVLVM  PLSIIYIVMD  .RWKLGYFLC
    5HT1A       IALERSLQNV   ANYLIGSLAV  TDLMVSVLVL  PMAALYQVLN  .KWTLGQVTC
TM Region       *.........  ...*******  ***..II..*  *******..   ..........

151                                                            200
    5HT1C       PVWISLDVLF   STASIMHLCA  ISLDRYVAIR  NPIEHSRFNS  RTKAIMKIAI
    5HT2        AVWIYLDVLF   STASIMHLCA  ISLDRYVAIQ  NPIHHSRFNS  RTKAFLKIIA
    5HT1Dα      DIWLSSDITC   CTASILHLCV  IALDRYWAIT  DALEYSKRRT  AGHAATMIAI
    5HT1Dβ      DFWLSSDITC   CTASILHLCV  IALDRYWAIT  DAVEYSAKRT  PKRAAVMIAL
    5HT1E       EVWLSVDMTC   CTCSILHLCV  IALDRYWAIT  NAIEYARKRT  AKRAALMILT
    5HT1A       DLFIALDVLC   CTSSILHLCA  IALDRYWAIT  DPIDYVNKRT  PRRAAALISL
TM Region       .********.   .III..****  ***.......  ..........  ......****

201                                                            250
    5HT1C       VWAISIGVSV   PIPVIGLRDE  SKVFVNNTTC  VLNDPNFVLI  GSFVAFFIPL
    5HT2        VWTISVGISM   PIPVFGLQDD  SKVF.KEGSC  LLADDNFVLI  GSFVSFFIPL
    5HT1Dα      VWAISICISI   PPLFWR.QEK  AQEEMSDCLV  NTSQISYTIY  STCGAFYIPS
    5HT1Dβ      VWVFSISISL   PPFFWR.QAK  AEEEVSECVV  NTDHILYTVY  STVGAFYFPT
    5HT1E       VWTISIFISM   PPLFWRSHRR  LSPPPSQCTI  QHDHVIYTIY  STLGAFYIPL
    5HT1A       TWLIGFLISI   PPMLGWRTPE  DRSDPDACTI  SKDH.GYTIY  STFGAFYIPL
TM Region       ****..IV..  ********..  ..........  ......****  *****...V..

251                                                            300
    5HT1C       TIMVITY...  ..........  ..........  ..........  ..........
    5HT2        TIMVITY...  ..........  ..........  ..........  ..........
    5HT1Dα      VLLIILYGRI   YRAAR.....  ..........  ..........  ..........
    5HT1Dβ      LLLIALYGRI   YVEAR.....  ..........  ..........  ..........
    5HT1E       TLILILYYRI   YHAAKSLYQK  R.........  ..........  ..........
    5HT1A       LLMLVYGRI    FRAARFRIRK  TVKKVEKTGA  DTRHGASPAP  QPKKSVNGES
TM Region       *******...  ..........  ..........  ..........  ..........
```

FIGURE 2B

```
            301                                                          350
5HT1C       .....FLTIY VLRRQTLMLL RG.HTEEELA NMSLNFLNCC CKKNGGEEEN
5HT2        .....FLTIK SLQKEATLCV SDLGTRAKLA ..SFSFLPQS SLSSEKLFQR
5HT1Dα      ...NRIL.NP PSLSGKRFTT AHLITGSAG. ..SVCSL... ..NSSLHEGH
5HT1Dβ      ...SRILKQT PNRTGKRLTR AQLITDSPGS TSSVTSI... ..NSRVPDVP
5HT1E       .GSSRHLSNR STDSQNSFAS CKLTQTFCVS DFSTSDP... ..TTEFEKFH
5HT1A       GSRNWRLGVE SKAGGALCAN GAVRQGDDGA ALEVIEVHRV GNSKEHLPLP
TM Region   .......... .......... .......... .......... ..........

351                                                          400
5HT1C       APNPNPDQKP RR...KKKEK RPRGTMQAIN NEKKASKVLG IVFFVFLIMW
5HT2        SIHREPGSYT GR...R.... ....TMQSIS NEQKACKVLG IVFFLFVVMW
5HT1Dα      SHSAGSPLFF NHVKIKLADS ALERKRISAA RERKATKILG IILGAFIICW
5HT1Dβ      SES.GSPVYV NQVKVRVSDA LLEKKKLMAA RERKATKTLG IILGAFIVCW
5HT1E       A.SIRIPPFD NDL.....DH PGERQQISST RERKAARILG LILGAFILSW
5HT1A       SEAGPTPCAP ASFERKNERN AEAKRKMALA RERKTVKTLG IIMGTFILCW
TM Region   .......... .......... .......... ......... *****..V 401                                                          450
5HT1C       CPFFITNILS VLCGKACNQK LMEKLLNVFV WIGYVCSGIN PLVYTLFNKI
5HT2        CPFFITNIMA VICKESCNED VIGALLNVFV WIGYLSSAVN PLVYTLFNKT
5HT1Dα      LPFFVVSLVL PICRDSCWIH P..GLFDFFT WLGYLNSLIN PIIYTVFNEE
5HT1Dβ      LPFFIISLVM PICKDACWFH L..AIFDFFT WLGYLNSLIN PIIYTMSNED
5HT1E       LPFFIKELIV GLSIYTVSSE V..A..DFLT WLGYVNSLIN PLLYTSFNED
5HT1A       LPFFIVALVL PFCESSCHMP T..LLGAIIN WLGYSNSLLN PVIYAYFNKD
TM Region   I..******* *......... ..******** **..VII..* *******...

451                                                          500
5HT1C       YRRAFSKYLR CDYKPDKKP. PVRQIPRVAA TALSGRELNV NIYRHTNERV
5HT2        YRSAFSRYIQ CQYKENKKPL QLILVNTIPA LAYKSSQLQM GQKKNSKQDA
5HT1Dα      FRQAFQKIVP FRKA...... .......... .......... ..........
5HT1Dβ      FKQAFHKLIR LSAQVDLPFA VGP....... .......... ..........
5HT1E       FKLAFKKLIR CREHT..... .......... .......... ..........
5HT1A       FQNAFKKIIK CLFCRQ*.... .......... .......... ..........
TM Region   .......... .......... .......... .......... ..........

501                                  536
5HT1C       ARKANDPEPG IEMQVENLEL PVNPSNVVSE RISSV*
5HT2        KTTDNDCSMV ALGKQHSEEA SKDNSDGVNE KVSCV*
5HT1Dα      .......... .......... .......... ......
5HT1Dβ      .......... .......... .......... ......
5HT1E       .......... .......... .......... ......
5HT1A       .......... .......... .......... ......
TM Region   .......... .......... .......... ......
```

FIGURE 5

| Brain Tissues | 5-HT$_{1E}$ | | |
|---|---|---|---|
| | Experiment 1 | Experiment 2 | Experiment 3 |
| Frontal Cortex | + | + | + |
| Cerebellar Cortex | + + | + | + + |
| Temporal Cortex | + | + + | + + + |
| Choroid Plexus | + + + | + + | + + + |
| Hippocampus | + + + | + + | + + + |
| Brain Stem | + | + + | + + + |
| Cortex | + + | + + | + + + |
| (+) Control | + + + | + + + | + + + |
| (-) Control | - | - | - |

Figure Key:
+ + + = dark
+ + = light
+ = present but faint
- = absent

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2463 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i i ) IMMEDIATE SOURCE:
        ( A ) LIBRARY: human placental genomic
        ( B ) CLONE: hp75d ( v i i i ) POSITION IN GENOME:
        ( C ) UNITS: bp ( i x ) FEATURE:
        ( A ) NAME/KEY: CDS
        ( B ) LOCATION: 736..1830

( i x ) FEATURE:
        ( A ) NAME/KEY: mat_peptide
        ( B ) LOCATION: 736..1830

( x i ) SEQUENCE DESCRIPTION: SEQ ID NO:1:

```
ATATACATCA   TGGAATACTA   TGCAGCCCCC   CCCAAGGATG   CGTTCCATGT   CCTTTGCAGG         60

GACATGGATG   AGTTGCAAAC   CATATTCTCA   ACAAACTAAC   ACAGCCACAG   AAAACCAAAC        120

ACCACATGCT   CTCACTCACG   AGTGGAGTTG   AACAATGAGA   ACACATGGCA   CAGGGCCGGG        180

AACATGACAC   ACCAGGGCCT   GTTGGGGGGT   GGAGGGCTAG   GGGAGGGATG   GCATTAGGAG        240
```

```
AAGTACCTAA TGTAGATGAT TGGTTGTTGG GTGCAGCAAA CCACCATGGC ACATGTATAC        300

CTATGTAGCA AACCTGCAAG TTCTGCACAT GTATCCCAGG ACTTAAAGTA TAATTTAAAA        360

AAAAACAGTT TGAAAACTTC CCTGAAGTAA AAAAGTATC CTTTGAGGAA CAATGTAACG         420

ATGAGCTCAA GTTCCACAGG AAAGAGAAAA TTAAAATTTA TAAAGAATTT ATAAATATCA       480

AACTATTTTC ATGTTTTCCA GGAAAAGTGT GGCTTTCTCA TTCATTAACC AATAGCATAA       540

TATTTTCCAG GAACCTTCAC TCAGAAGAAA TGCTGTGGCC CTTCCCTTTA CCAACAGAAA      600

ATGGAACACA AGAGACCACA TAGCTGAACA AATTATAGCC TCCTTACAAG TGAGAAACCT      660

TCGAGGCTAC ATAGTTTTCA GCCAAGGAA AATAACCAAC AGCTTCTCCA CAGTGTAGAC       720
```

| | | | | | | | | | | | | | | | | |
|---|---|---|---|---|---|---|---|---|---|---|---|---|---|---|---|---|
| TGAAACAAGG GAAAC | ATG | AAC | ATC | ACA | AAC | TGT | ACC | ACA | GAG | GCC | AGC | ATG | | | | 771 |
| | Met | Asn | Ile | Thr | Asn | Cys | Thr | Thr | Glu | Ala | Ser | Met | | | | |
| | 1 | | | 5 | | | | | | 10 | | | | | | |
| GCT | ATA | AGA | CCC | AAG | ACC | ATC | ACT | GAG | AAG | ATG | CTC | ATT | TGC | ATG | ACT | 819 |
| Ala | Ile | Arg | Pro | Lys | Thr | Ile | Thr | Glu | Lys | Met | Leu | Ile | Cys | Met | Thr | |
| | | 15 | | | | 20 | | | | | 25 | | | | | |
| CTG | GTG | GTC | ATC | ACC | ACC | CTC | ACC | ACG | TTG | CTG | AAC | TTG | GCT | GTG | ATC | 867 |
| Leu | Val | Val | Ile | Thr | Thr | Leu | Thr | Thr | Leu | Leu | Asn | Leu | Ala | Val | Ile | |
| | 30 | | | | | 35 | | | | 40 | | | | | | |
| ATG | GCT | ATT | GGC | ACC | ACC | AAG | AAG | CTC | CAC | CAG | CCT | GCC | AAC | TAC | CTA | 915 |
| Met | Ala | Ile | Gly | Thr | Thr | Lys | Lys | Leu | His | Gln | Pro | Ala | Asn | Tyr | Leu | |
| 45 | | | | | 50 | | | | | 55 | | | | | 60 | |
| ATC | TGT | TCT | CTG | GCC | GTG | ACG | GAC | CTC | CTG | GTG | GCA | GTG | CTC | GTC | ATG | 963 |
| Ile | Cys | Ser | Leu | Ala | Val | Thr | Asp | Leu | Leu | Val | Ala | Val | Leu | Val | Met | |
| | | | | | 65 | | | | | 70 | | | | | 75 | |
| CCC | CTG | AGC | ATC | ATC | TAC | ATT | GTC | ATG | GAT | CGC | TGG | AAG | CTT | GGG | TAC | 1011 |
| Pro | Leu | Ser | Ile | Ile | Tyr | Ile | Val | Met | Asp | Arg | Trp | Lys | Leu | Gly | Tyr | |
| | | | 80 | | | | | 85 | | | | | 90 | | | |
| TTC | CTC | TGT | GAG | GTG | TGG | CTG | AGT | GTG | GAC | ATG | ACC | TGC | TGC | ACC | TGC | 1059 |
| Phe | Leu | Cys | Glu | Val | Trp | Leu | Ser | Val | Asp | Met | Thr | Cys | Cys | Thr | Cys | |
| | | 95 | | | | | 100 | | | | | 105 | | | | |
| TCC | ATC | CTC | CAC | CTC | TGT | GTC | ATT | GCC | CTG | GAC | AGG | TAC | TGG | GCC | ATC | 1107 |
| Ser | Ile | Leu | His | Leu | Cys | Val | Ile | Ala | Leu | Asp | Arg | Tyr | Trp | Ala | Ile | |
| | 110 | | | | | 115 | | | | | 120 | | | | | |
| ACC | AAT | GCT | ATT | GAA | TAC | GCC | AGG | AAG | AGG | ACG | GCC | AAG | AGG | GCC | GCG | 1155 |
| Thr | Asn | Ala | Ile | Glu | Tyr | Ala | Arg | Lys | Arg | Thr | Ala | Lys | Arg | Ala | Ala | |
| 125 | | | | | 130 | | | | | 135 | | | | | 140 | |
| CTG | ATG | ATC | CTT | ACC | GTC | TGG | ACC | ATC | TCC | ATT | TTC | ATC | TCC | ATG | CCC | 1203 |
| Leu | Met | Ile | Leu | Thr | Val | Trp | Thr | Ile | Ser | Ile | Phe | Ile | Ser | Met | Pro | |
| | | | | | 145 | | | | | 150 | | | | | 155 | |
| CCT | CTG | TTC | TGG | AGA | AGC | CAC | CGC | CGC | CTA | AGC | CCT | CCC | CCT | AGT | CAG | 1251 |
| Pro | Leu | Phe | Trp | Arg | Ser | His | Arg | Arg | Leu | Ser | Pro | Pro | Pro | Ser | Gln | |
| | | | 160 | | | | | 165 | | | | | 170 | | | |
| TGC | ACC | ATC | CAG | CAC | GAC | CAT | GTT | ATC | TAC | ACC | ATT | TAC | TCC | ACG | CTG | 1299 |
| Cys | Thr | Ile | Gln | His | Asp | His | Val | Ile | Tyr | Thr | Ile | Tyr | Ser | Thr | Leu | |
| | | 175 | | | | | 180 | | | | | 185 | | | | |
| GGT | GCG | TTT | TAT | ATC | CCC | TTG | ACT | TTG | ATA | CTG | ATT | CTC | TAT | TAC | CGG | 1347 |
| Gly | Ala | Phe | Tyr | Ile | Pro | Leu | Thr | Leu | Ile | Leu | Ile | Leu | Tyr | Tyr | Arg | |
| | 190 | | | | | 195 | | | | | 200 | | | | | |
| ATT | TAC | CAC | GCG | GCC | AAG | AGC | CTT | TAC | CAG | AAA | AGG | GGA | TCA | AGT | CGG | 1395 |
| Ile | Tyr | His | Ala | Ala | Lys | Ser | Leu | Tyr | Gln | Lys | Arg | Gly | Ser | Ser | Arg | |
| 205 | | | | | 210 | | | | | 215 | | | | | 220 | |
| CAC | TTA | AGC | AAC | AGA | AGC | ACA | GAT | AGC | CAG | AAT | TCT | TTT | GCA | AGT | TGT | 1443 |
| His | Leu | Ser | Asn | Arg | Ser | Thr | Asp | Ser | Gln | Asn | Ser | Phe | Ala | Ser | Cys | |
| | | | | 225 | | | | | 230 | | | | | 235 | | |
| AAA | CTT | ACA | CAG | ACT | TTC | TGT | GTG | TCT | GAC | TTC | TCC | ACC | TCA | GAC | CCT | 1491 |
| Lys | Leu | Thr | Gln | Thr | Phe | Cys | Val | Ser | Asp | Phe | Ser | Thr | Ser | Asp | Pro | |

|  |  |  |  |  |  |  | 240 |  |  |  |  |  | 245 |  |  |  |  |  | 250 |  |  |  |  |  |  |
|---|---|---|---|---|---|---|---|---|---|---|---|---|---|---|---|---|---|---|---|---|---|---|---|---|---|

```
ACC  ACA  GAG  TTT  GAA  AAG  TTC  CAT  GCC  TCC  ATC  AGG  ATC  CCC  CCC  TTC          1539
Thr  Thr  Glu  Phe  Glu  Lys  Phe  His  Ala  Ser  Ile  Arg  Ile  Pro  Pro  Phe
          255                      260                      265

GAC  AAT  GAT  CTA  GAT  CAC  CCA  GGA  GAA  CGT  CAG  CAG  ATC  TCT  AGC  ACC          1587
Asp  Asn  Asp  Leu  Asp  His  Pro  Gly  Glu  Arg  Gln  Gln  Ile  Ser  Ser  Thr
          270                      275                      280

AGG  GAA  CGG  AAG  GCA  GCA  CGC  ATC  CTG  GGG  CTG  ATT  CTG  GGT  GCA  TTC          1635
Arg  Glu  Arg  Lys  Ala  Ala  Arg  Ile  Leu  Gly  Leu  Ile  Leu  Gly  Ala  Phe
285                 290                      295                      300

ATT  TTA  TCC  TGG  CTG  CCA  TTT  TTC  ATC  AAA  GAG  TTG  ATT  GTG  GGT  CTG          1683
Ile  Leu  Ser  Trp  Leu  Pro  Phe  Phe  Ile  Lys  Glu  Leu  Ile  Val  Gly  Leu
               305                      310                      315

AGC  ATC  TAC  ACC  GTG  TCC  TCG  GAA  GTG  GCC  GAC  TTT  CTG  ACG  TGG  CTC          1731
Ser  Ile  Tyr  Thr  Val  Ser  Ser  Glu  Val  Ala  Asp  Phe  Leu  Thr  Trp  Leu
                    320                      325                      330

GGT  TAT  GTG  AAT  TCT  CTG  ATC  AAC  CCT  CTG  CTC  TAT  ACG  AGT  TTT  AAT          1779
Gly  Tyr  Val  Asn  Ser  Leu  Ile  Asn  Pro  Leu  Leu  Tyr  Thr  Ser  Phe  Asn
               335                      340                      345

GAA  GAC  TTT  AAG  CTG  GCT  TTT  AAA  AAG  CTC  ATT  AGA  TGC  CGA  GAG  CAT          1827
Glu  Asp  Phe  Lys  Leu  Ala  Phe  Lys  Lys  Leu  Ile  Arg  Cys  Arg  Glu  His
     350                      355                      360

ACT  TAGACTGTAA AAAGCTAAAA GGCACGACTT TTTCCAGAGC CTCATGAGTG                              1880
Thr
365

GATGGGGGTA AGGGGTGCAA CTTATTAATT CTTGAACATA CTTGGTTCAG GAGAGTTTGT                        1940

AAGTATGTGT GGTCTTGTTT CCTTGTTTGT TTGTTTGTTT TGTTCTGTTT TGTTTGAGGA                        2000

TTGTTATTTG GCCTCCTGTT TTCTACCTCT GGTCTTATCT GTGATACATA ATTTCAAATA                        2060

AACATTATCA TACAAAAACA GAAATTTTGC CAGAAGTAAT AATAAGATGA AATACTAAAT                        2120

ACCTTTTATG GGTTTTTTTT TTTTAGCCAT TTCAGTTACC CTGCAATTAA AGAATGCCAA                        2180

AAATATCTTT ATTTGCAGAA TTTCTTATTA CTTATAAATT AAATACCTGA TAATGCCCTC                        2240

CATGGCATTA AATCTGAGAT TATGGCTCTA TCTGCGTACA TATTCCAGTG GGAATTGCAT                        2300

GACTACATAA AGAATTAAAA GAAAGTGATG TGCTGTCATC TACGGCTTGC GACCTGAGCT                        2360

AAAGTCGGGG GCTGTAGCAC TGTGACTACG TAGCCTATCA TTTCAGGTAA AAATAGTACA                        2420

GCTGGCTTGT CTTGTTAGTT CATGATTAAA TAAACTTCTC TTT                                         2463
```

( 2 ) INFORMATION FOR SEQ ID NO:2:

( i ) SEQUENCE CHARACTERISTICS:
        ( A ) LENGTH: 365 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asn  Ile  Thr  Asn  Cys  Thr  Thr  Glu  Ala  Ser  Met  Ala  Ile  Arg  Pro
1                 5                        10                       15

Lys  Thr  Ile  Thr  Glu  Lys  Met  Leu  Ile  Cys  Met  Thr  Leu  Val  Val  Ile
               20                       25                       30

Thr  Thr  Leu  Thr  Thr  Leu  Leu  Asn  Leu  Ala  Val  Ile  Met  Ala  Ile  Gly
          35                       40                       45

Thr  Thr  Lys  Lys  Leu  His  Gln  Pro  Ala  Asn  Tyr  Leu  Ile  Cys  Ser  Leu
     50                       55                       60

Ala  Val  Thr  Asp  Leu  Leu  Val  Ala  Val  Leu  Val  Met  Pro  Leu  Ser  Ile
```

|   | 65 |   |   |   |   | 70 |   |   |   |   | 75 |   |   |   |   | 80 |
|---|---|---|---|---|---|---|---|---|---|---|---|---|---|---|---|---|

Ile Tyr Ile Val Met Asp Arg Trp Lys Leu Gly Tyr Phe Leu Cys Glu
                85                  90                  95

Val Trp Leu Ser Val Asp Met Thr Cys Thr Cys Ser Ile Leu His
               100             105             110

Leu Cys Val Ile Ala Leu Asp Arg Tyr Trp Ala Ile Thr Asn Ala Ile
           115             120             125

Glu Tyr Ala Arg Lys Arg Thr Ala Lys Arg Ala Ala Leu Met Ile Leu
130             135             140

Thr Val Trp Thr Ile Ser Ile Phe Ile Ser Met Pro Pro Leu Phe Trp
145             150             155             160

Arg Ser His Arg Arg Leu Ser Pro Pro Ser Gln Cys Thr Ile Gln
               165             170             175

His Asp His Val Ile Tyr Thr Ile Tyr Ser Thr Leu Gly Ala Phe Tyr
           180             185             190

Ile Pro Leu Thr Leu Ile Leu Ile Leu Tyr Tyr Arg Ile Tyr His Ala
           195             200             205

Ala Lys Ser Leu Tyr Gln Lys Arg Gly Ser Ser Arg His Leu Ser Asn
210             215             220

Arg Ser Thr Asp Ser Gln Asn Ser Phe Ala Ser Cys Lys Leu Thr Gln
225             230             235             240

Thr Phe Cys Val Ser Asp Phe Ser Thr Ser Asp Pro Thr Thr Glu Phe
               245             250             255

Glu Lys Phe His Ala Ser Ile Arg Ile Pro Pro Phe Asp Asn Asp Leu
           260             265             270

Asp His Pro Gly Glu Arg Gln Gln Ile Ser Ser Thr Arg Glu Arg Lys
           275             280             285

Ala Ala Arg Ile Leu Gly Leu Ile Leu Gly Ala Phe Ile Leu Ser Trp
290             295             300

Leu Pro Phe Phe Ile Lys Glu Leu Ile Val Gly Leu Ser Ile Tyr Thr
305             310             315             320

Val Ser Ser Glu Val Ala Asp Phe Leu Thr Trp Leu Gly Tyr Val Asn
               325             330             335

Ser Leu Ile Asn Pro Leu Leu Tyr Thr Ser Phe Asn Glu Asp Phe Lys
           340             345             350

Leu Ala Phe Lys Lys Leu Ile Arg Cys Arg Glu His Thr
           355             360             365

(2) INFORMATION FOR SEQ ID NO:3:

(i) SEQUENCE CHARACTERISTICS:
        (A) LENGTH: 422 amino acids
        (B) TYPE: amino acid
        (C) STRANDEDNESS: unknown
        (D) TOPOLOGY: unknown (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:3:

Met Asp Val Leu Ser Pro Gly Gln Gly Asn Asn Thr Thr Ser Pro Pro
1               5                   10                  15

Ala Pro Phe Glu Thr Gly Gly Asn Thr Thr Gly Ile Ser Asp Val Thr

|  |  |  |  |  |  |  |  |  |  |  |  |  |  |
|---|---|---|---|---|---|---|---|---|---|---|---|---|---|
|  |  |  | 20 |  |  |  | 25 |  |  |  | 30 |  |  |
| Val | Ser | Tyr 35 | Gln | Val | Ile | Thr | Ser 40 | Leu | Leu | Leu | Gly | Thr 45 | Leu | Ile | Phe |
| Cys | Ala 50 | Val | Leu | Gly | Asn | Ala 55 | Cys | Val | Val | Ala | Ala 60 | Ile | Ala | Leu | Glu |
| Arg 65 | Ser | Leu | Gln | Asn | Val 70 | Ala | Asn | Tyr | Leu | Ile 75 | Gly | Ser | Leu | Ala | Val 80 |
| Thr | Asp | Leu | Met | Val 85 | Ser | Val | Leu | Val | Leu 90 | Pro | Met | Ala | Ala | Leu 95 | Tyr |
| Gln | Val | Leu | Asn 100 | Lys | Trp | Thr | Leu | Gly 105 | Gln | Val | Thr | Cys | Asp 110 | Leu | Phe |
| Ile | Ala | Leu 115 | Asp | Val | Leu | Cys | Cys 120 | Thr | Ser | Ser | Ile | Leu 125 | His | Leu | Cys |
| Ala | Ile 130 | Ala | Leu | Asp | Arg | Tyr 135 | Trp | Ala | Ile | Thr | Asp 140 | Pro | Ile | Asp | Tyr |
| Val 145 | Asn | Lys | Arg | Thr | Pro 150 | Arg | Arg | Ala | Ala | Ala 155 | Leu | Ile | Ser | Leu | Thr 160 |
| Trp | Leu | Ile | Gly | Phe 165 | Leu | Ile | Ser | Ile | Pro 170 | Pro | Met | Leu | Gly | Trp 175 | Arg |
| Thr | Pro | Glu | Asp 180 | Arg | Ser | Asp | Pro | Asp 185 | Ala | Cys | Thr | Ile | Ser 190 | Lys | Asp |
| His | Gly | Tyr 195 | Thr | Ile | Tyr | Ser | Thr 200 | Phe | Gly | Ala | Phe | Tyr 205 | Ile | Pro | Leu |
| Leu | Leu 210 | Met | Leu | Val | Leu | Tyr 215 | Gly | Arg | Ile | Phe | Arg 220 | Ala | Ala | Arg | Phe |
| Arg 225 | Ile | Arg | Lys | Thr | Val 230 | Lys | Lys | Val | Glu | Lys 235 | Thr | Gly | Ala | Asp | Thr 240 |
| Arg | His | Gly | Ala | Ser 245 | Pro | Ala | Pro | Gln | Pro 250 | Lys | Lys | Ser | Val | Asn 255 | Gly |
| Glu | Ser | Gly | Ser 260 | Arg | Asn | Trp | Arg | Leu 265 | Gly | Val | Glu | Ser | Lys 270 | Ala | Gly |
| Gly | Ala | Leu 275 | Cys | Ala | Asn | Gly | Ala 280 | Val | Arg | Gln | Gly | Asp 285 | Asp | Gly | Ala |
| Ala | Leu 290 | Glu | Val | Ile | Glu | Val 295 | His | Arg | Val | Gly | Asn 300 | Ser | Lys | Glu | His |
| Leu 305 | Pro | Leu | Pro | Ser | Glu 310 | Ala | Gly | Pro | Thr | Pro 315 | Cys | Ala | Pro | Ala | Ser 320 |
| Phe | Glu | Arg | Lys | Asn 325 | Glu | Arg | Asn | Ala | Glu 330 | Ala | Lys | Arg | Lys | Met 335 | Ala |
| Leu | Ala | Arg | Glu 340 | Arg | Lys | Thr | Val | Lys 345 | Thr | Leu | Gly | Ile | Ile 350 | Met | Gly |
| Thr | Phe | Ile 355 | Leu | Cys | Trp | Leu | Pro 360 | Phe | Phe | Ile | Val | Ala 365 | Leu | Val | Leu |
| Pro | Phe 370 | Cys | Glu | Ser | Ser | Cys 375 | His | Met | Pro | Thr | Leu 380 | Leu | Gly | Ala | Ile |
| Ile 385 | Asn | Trp | Leu | Gly | Tyr 390 | Ser | Asn | Ser | Leu | Leu 395 | Asn | Pro | Val | Ile | Tyr 400 |
| Ala | Tyr | Phe | Asn | Lys 405 | Asp | Phe | Gln | Asn | Ala 410 | Phe | Lys | Lys | Ile | Ile 415 | Lys |
| Cys | Leu | Phe | Cys 420 | Arg | Gln |

( 2 ) INFORMATION FOR SEQ ID NO:4:

( i ) SEQUENCE CHARACTERISTICS:
  ( A ) LENGTH: 460 amino acids
  ( B ) TYPE: amino acid
  ( C ) STRANDEDNESS: unknown
  ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

| Met | Val | Asn | Leu | Gly | Asn | Ala | Val | Arg | Ser | Leu | Leu | Met | His | Leu | Ile |
|---|---|---|---|---|---|---|---|---|---|---|---|---|---|---|---|
| 1 | | | | 5 | | | | | 10 | | | | | 15 | |
| Gly | Leu | Leu | Val | Trp | Gln | Phe | Asp | Ile | Ser | Ile | Ser | Pro | Val | Ala | Ala |
| | | | 20 | | | | | 25 | | | | | 30 | | |
| Ile | Val | Thr | Asp | Thr | Phe | Asn | Ser | Ser | Asp | Gly | Gly | Arg | Leu | Phe | Gln |
| | | 35 | | | | | 40 | | | | | 45 | | | |
| Phe | Pro | Asp | Gly | Val | Gln | Asn | Trp | Pro | Ala | Leu | Ser | Ile | Val | Val | Ile |
| | 50 | | | | | 55 | | | | | 60 | | | | |
| Ile | Ile | Met | Thr | Ile | Gly | Gly | Asn | Ile | Leu | Val | Ile | Met | Ala | Val | Ser |
| 65 | | | | | 70 | | | | | 75 | | | | | 80 |
| Met | Glu | Lys | Lys | Leu | His | Asn | Ala | Thr | Asn | Tyr | Phe | Leu | Met | Ser | Leu |
| | | | | 85 | | | | | 90 | | | | | 95 | |
| Ala | Ile | Ala | Asp | Met | Leu | Val | Gly | Leu | Leu | Val | Met | Pro | Leu | Ser | Leu |
| | | | | 100 | | | | | 105 | | | | | 110 | |
| Leu | Ala | Ile | Leu | Tyr | Asp | Tyr | Val | Trp | Pro | Leu | Pro | Arg | Tyr | Leu | Cys |
| | | | 115 | | | | | 120 | | | | | 125 | | |
| Pro | Val | Trp | Ile | Ser | Leu | Asp | Val | Leu | Phe | Ser | Thr | Ala | Ser | Ile | Met |
| | | 130 | | | | | 135 | | | | | 140 | | | |
| His | Leu | Cys | Ala | Ile | Ser | Leu | Asp | Arg | Tyr | Val | Ala | Ile | Arg | Asn | Pro |
| 145 | | | | | 150 | | | | | 155 | | | | | 160 |
| Ile | Glu | His | Ser | Arg | Phe | Asn | Ser | Arg | Thr | Lys | Ala | Ile | Met | Lys | Ile |
| | | | | 165 | | | | | 170 | | | | | 175 | |
| Ala | Ile | Val | Trp | Ala | Ile | Ser | Ile | Gly | Val | Ser | Val | Pro | Ile | Pro | Val |
| | | | 180 | | | | | 185 | | | | | 190 | | |
| Ile | Gly | Leu | Arg | Asp | Glu | Ser | Lys | Val | Phe | Val | Asn | Asn | Thr | Thr | Cys |
| | | 195 | | | | | 200 | | | | | 205 | | | |
| Val | Leu | Asn | Asp | Pro | Asn | Phe | Val | Leu | Ile | Gly | Ser | Phe | Val | Ala | Phe |
| | 210 | | | | | 215 | | | | | 220 | | | | |
| Phe | Ile | Pro | Leu | Thr | Ile | Met | Val | Ile | Thr | Tyr | Phe | Leu | Thr | Ile | Tyr |
| 225 | | | | | 230 | | | | | 235 | | | | | 240 |
| Val | Leu | Arg | Arg | Gln | Thr | Leu | Met | Leu | Leu | Arg | Gly | His | Thr | Glu | Glu |
| | | | | 245 | | | | | 250 | | | | | 255 | |
| Glu | Leu | Ala | Asn | Met | Ser | Leu | Asn | Phe | Leu | Asn | Cys | Cys | Cys | Lys | Lys |
| | | | | 260 | | | | | 265 | | | | | 270 | |
| Asn | Gly | Gly | Glu | Glu | Asn | Ala | Pro | Asn | Pro | Asn | Pro | Asp | Gln | Lys |
| | | 275 | | | | | 280 | | | | | 285 | | | |
| Pro | Arg | Arg | Lys | Lys | Lys | Glu | Lys | Arg | Pro | Arg | Gly | Thr | Met | Gln | Ala |
| | | 290 | | | | | 295 | | | | | 300 | | | |
| Ile | Asn | Asn | Glu | Lys | Lys | Ala | Ser | Lys | Val | Leu | Gly | Ile | Val | Phe | Phe |
| 305 | | | | | 310 | | | | | 315 | | | | | 320 |
| Val | Phe | Leu | Ile | Met | Trp | Cys | Pro | Phe | Phe | Ile | Thr | Asn | Ile | Leu | Ser |
| | | | | 325 | | | | | 330 | | | | | 335 | |

```
Val  Leu  Cys  Gly  Lys  Ala  Cys  Asn  Gln  Lys  Leu  Met  Glu  Lys  Leu  Leu
               340                      345                     350

Asn  Val  Phe  Val  Trp  Ile  Gly  Tyr  Val  Cys  Ser  Gly  Ile  Asn  Pro  Leu
               355                      360                     365

Val  Tyr  Thr  Leu  Phe  Asn  Lys  Ile  Tyr  Arg  Arg  Ala  Phe  Ser  Lys  Tyr
               370                      375                     380

Leu  Arg  Cys  Asp  Tyr  Lys  Pro  Asp  Lys  Lys  Pro  Pro  Val  Arg  Gln  Ile
385                           390                     395                     400

Pro  Arg  Val  Ala  Ala  Thr  Ala  Leu  Ser  Gly  Arg  Glu  Leu  Asn  Val  Asn
               405                      410                     415

Ile  Tyr  Arg  His  Thr  Asn  Glu  Arg  Val  Ala  Arg  Lys  Ala  Asn  Asp  Pro
               420                      425                     430

Glu  Pro  Gly  Ile  Glu  Met  Gln  Val  Glu  Asn  Leu  Glu  Leu  Pro  Val  Asn
               435                      440                     445

Pro  Ser  Asn  Val  Val  Ser  Glu  Arg  Ile  Ser  Ser  Val
     450                      455                     460
```

( 2 ) INFORMATION FOR SEQ ID NO:5:

( i ) SEQUENCE CHARACTERISTICS:
        ( A ) LENGTH: 375 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

```
Met  Ser  Pro  Leu  Asn  Gln  Ser  Ala  Glu  Gly  Leu  Pro  Gln  Glu  Ala  Ser
1                        5                       10                      15

Asn  Arg  Ser  Leu  Asn  Ala  Thr  Glu  Thr  Ser  Glu  Ala  Trp  Asp  Pro  Arg
               20                       25                      30

Thr  Leu  Gln  Ala  Leu  Lys  Ile  Ser  Leu  Pro  Val  Leu  Leu  Ser  Val  Ile
               35                       40                      45

Thr  Leu  Ala  Thr  Val  Leu  Ser  Asn  Ala  Phe  Val  Leu  Thr  Thr  Ile  Leu
     50                       55                      60

Leu  Thr  Arg  Lys  Leu  His  Thr  Pro  Ala  Asn  Tyr  Leu  Ile  Gly  Ser  Leu
65                       70                      75                      80

Ala  Thr  Thr  Asp  Leu  Leu  Val  Ser  Ile  Leu  Val  Met  Pro  Ile  Ser  Met
                    85                       90                      95

Ala  Tyr  Thr  Ile  Thr  His  Thr  Trp  Asn  Phe  Gly  Gln  Ile  Leu  Cys  Asp
               100                      105                     110

Ile  Trp  Leu  Ser  Ser  Asp  Ile  Thr  Cys  Cys  Thr  Ala  Ser  Ile  Leu  His
               115                      120                     125

Leu  Cys  Val  Ile  Ala  Leu  Asp  Arg  Tyr  Trp  Ala  Ile  Thr  Asp  Ala  Leu
     130                      135                     140

Glu  Tyr  Ser  Lys  Arg  Arg  Thr  Ala  Gly  His  Ala  Ala  Thr  Met  Ile  Ala
145                      150                     155                     160

Ile  Val  Trp  Ala  Ile  Ser  Ile  Cys  Ile  Ser  Ile  Pro  Pro  Leu  Phe  Trp
                    165                      170                     175

Arg  Gln  Glu  Lys  Ala  Gln  Glu  Glu  Met  Ser  Asp  Cys  Leu  Val  Asn  Thr
               180                      185                     190
```

```
Ser  Gln  Ile  Ser  Tyr  Thr  Ile  Tyr  Ser  Thr  Cys  Gly  Ala  Phe  Tyr  Ile
     195                      200                      205

Pro  Ser  Val  Leu  Leu  Ile  Ile  Leu  Tyr  Gly  Arg  Ile  Tyr  Arg  Ala  Ala
     210                      215                      220

Arg  Asn  Arg  Ile  Leu  Asn  Pro  Pro  Ser  Leu  Ser  Gly  Lys  Arg  Phe  Thr
225                           230                 235                      240

Thr  Ala  His  Leu  Ile  Thr  Gly  Ser  Ala  Gly  Ser  Val  Cys  Ser  Leu  Asn
               245                      250                           255

Ser  Ser  Leu  His  Glu  Gly  His  Ser  His  Ser  Ala  Gly  Ser  Pro  Leu  Phe
               260                      265                      270

Phe  Asn  His  Val  Lys  Ile  Lys  Leu  Ala  Asp  Ser  Ala  Leu  Glu  Arg  Lys
          275                      280                      285

Arg  Ile  Ser  Ala  Ala  Arg  Glu  Arg  Lys  Ala  Thr  Lys  Ile  Leu  Gly  Ile
     290                      295                      300

Ile  Leu  Gly  Ala  Phe  Ile  Ile  Cys  Trp  Leu  Pro  Phe  Phe  Val  Val  Ser
305                           310                      315                 320

Leu  Val  Leu  Pro  Ile  Cys  Arg  Asp  Ser  Cys  Trp  Ile  His  Pro  Gly  Leu
                325                      330                           335

Phe  Asp  Phe  Phe  Thr  Trp  Leu  Gly  Tyr  Leu  Asn  Ser  Leu  Ile  Asn  Pro
               340                      345                      350

Ile  Ile  Tyr  Thr  Val  Phe  Asn  Glu  Glu  Phe  Arg  Gln  Ala  Phe  Gln  Lys
          355                      360                      365

Ile  Val  Pro  Phe  Arg  Lys  Ala
     370                      375
```

( 2 ) INFORMATION FOR SEQ ID NO:6:

( i ) SEQUENCE CHARACTERISTICS:
        ( A ) LENGTH: 398 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

```
Met  Glu  Glu  Pro  Gly  Ala  Gln  Cys  Ala  Pro  Pro  Ala  Pro  Ala  Gly  Ser
1                   5                   10                      15

Glu  Thr  Trp  Val  Pro  Gln  Ala  Asn  Leu  Ser  Ser  Ala  Pro  Ser  Gln  Asn
               20                      25                      30

Cys  Ser  Ala  Lys  Asp  Tyr  Ile  Tyr  Gln  Asp  Ser  Ile  Ser  Leu  Pro  Trp
          35                      40                      45

Lys  Val  Leu  Leu  Val  Met  Leu  Leu  Ala  Leu  Ile  Thr  Leu  Ala  Thr  Thr
     50                      55                      60

Leu  Ser  Asn  Ala  Phe  Val  Ile  Ala  Thr  Val  Tyr  Arg  Thr  Arg  Lys  Leu
65                       70                      75                       80

His  Thr  Pro  Ala  Asn  Tyr  Leu  Ile  Ala  Ser  Leu  Asp  Val  Thr  Asp  Leu
               85                      90                      95

Leu  Val  Ser  Ile  Leu  Val  Ile  Pro  Ile  Ser  Thr  Met  Tyr  Thr  Val  Thr
               100                     105                     110

Asp  Arg  Trp  Thr  Leu  Ser  Gln  Val  Val  Cys  Asp  Phe  Trp  Leu  Ser  Ser
               115                     120                     125
```

```
Asp  Ile  Thr  Cys  Cys  Thr  Ala  Ser  Ile  Leu  His  Leu  Cys  Val  Ile  Ala
     130                 135                      140

Leu  Asp  Arg  Tyr  Trp  Ala  Ile  Thr  Asp  Ala  Val  Glu  Tyr  Ser  Ala  Lys
145                      150                      155                      160

Arg  Thr  Pro  Lys  Arg  Ala  Ala  Val  Met  Ile  Ala  Leu  Val  Trp  Val  Phe
                    165                      170                      175

Ser  Ile  Ser  Ile  Ser  Leu  Pro  Pro  Phe  Phe  Trp  Arg  Gln  Ala  Lys  Ala
               180                      185                      190

Glu  Glu  Glu  Val  Ser  Glu  Cys  Val  Val  Asn  Thr  Asp  His  Ile  Leu  Tyr
          195                 200                      205

Thr  Val  Tyr  Ser  Thr  Val  Gly  Ala  Phe  Tyr  Phe  Pro  Thr  Leu  Leu  Leu
     210                      215                      220

Ile  Ala  Leu  Tyr  Gly  Arg  Ile  Tyr  Val  Glu  Ala  Arg  Ser  Arg  Ile  Leu
225                      230                      235                      240

Lys  Gln  Thr  Pro  Asn  Arg  Thr  Gly  Lys  Arg  Leu  Thr  Arg  Ala  Gln  Leu
                    245                      250                      255

Ile  Thr  Asp  Ser  Pro  Gly  Ser  Thr  Ser  Ser  Val  Thr  Ser  Ile  Asn  Ser
               260                      265                      270

Arg  Val  Pro  Asp  Val  Pro  Ser  Glu  Ser  Gly  Ser  Pro  Val  Tyr  Val  Asn
          275                      280                      285

Gln  Val  Lys  Val  Arg  Val  Ser  Asp  Ala  Leu  Leu  Glu  Lys  Lys  Lys  Leu
     290                      295                      300

Met  Ala  Ala  Arg  Glu  Arg  Lys  Ala  Thr  Lys  Thr  Leu  Gly  Ile  Ile  Leu
305                      310                      315                      320

Gly  Ala  Phe  Ile  Val  Cys  Trp  Leu  Pro  Phe  Phe  Ile  Ile  Ser  Leu  Val
                    325                      330                      335

Met  Pro  Ile  Cys  Lys  Asp  Ala  Cys  Trp  Phe  His  Leu  Ala  Ile  Phe  Asp
               340                      345                      350

Phe  Phe  Thr  Trp  Leu  Gly  Tyr  Leu  Asn  Ser  Leu  Ile  Asn  Pro  Ile  Ile
          355                      360                      365

Tyr  Thr  Met  Ser  Asn  Glu  Asp  Phe  Lys  Gln  Ala  Phe  His  Lys  Leu  Ile
     370                      375                      380

Arg  Leu  Ser  Ala  Gln  Val  Asp  Leu  Pro  Phe  Ala  Val  Gly  Pro
385                      390                      395
```

( 2 ) INFORMATION FOR SEQ ID NO:7:

( i ) SEQUENCE CHARACTERISTICS:
        ( A ) LENGTH: 471 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

```
Met  Asp  Ile  Leu  Cys  Glu  Glu  Asn  Thr  Ser  Leu  Ser  Ser  Thr  Thr  Asn
1                   5                   10                      15

Ser  Leu  Met  Gln  Leu  Asn  Asp  Asp  Thr  Arg  Leu  Tyr  Ser  Asn  Asp  Phe
               20                      25                      30

Asn  Ser  Gly  Glu  Ala  Asn  Thr  Ser  Asp  Ala  Phe  Asn  Trp  Thr  Val  Asp
          35                      40                      45
```

```
Ser  Glu  Asn  Arg  Thr  Asn  Leu  Ser  Cys  Glu  Gly  Cys  Leu  Ser  Pro  Ser
     50                  55                  60
Cys  Leu  Ser  Leu  Leu  His  Leu  Gln  Glu  Lys  Asn  Trp  Ser  Ala  Leu  Leu
65                  70                  75                                 80
Thr  Ala  Val  Val  Ile  Ile  Leu  Thr  Ile  Ala  Gly  Asn  Ile  Leu  Val  Ile
                    85                  90                       95
Met  Ala  Val  Ser  Leu  Glu  Lys  Lys  Leu  Gln  Asn  Ala  Thr  Asn  Tyr  Phe
               100                 105                      110
Leu  Met  Ser  Leu  Ala  Ile  Ala  Asp  Met  Leu  Leu  Gly  Phe  Leu  Val  Met
          115                 120                      125
Pro  Val  Ser  Met  Leu  Thr  Ile  Leu  Tyr  Gly  Tyr  Arg  Trp  Pro  Leu  Pro
     130                 135                      140
Ser  Lys  Leu  Cys  Ala  Val  Trp  Ile  Tyr  Leu  Asp  Val  Leu  Phe  Ser  Thr
145                      150                 155                           160
Ala  Ser  Ile  Met  His  Leu  Cys  Ala  Ile  Ser  Leu  Asp  Arg  Tyr  Val  Ala
               165                      170                      175
Ile  Gln  Asn  Pro  Ile  His  His  Ser  Arg  Phe  Asn  Ser  Arg  Thr  Lys  Ala
               180                      185                 190
Phe  Leu  Lys  Ile  Ile  Ala  Val  Trp  Thr  Ile  Ser  Val  Gly  Ile  Ser  Met
          195                 200                 205
Pro  Ile  Pro  Val  Phe  Gly  Leu  Gln  Asp  Asp  Ser  Lys  Val  Phe  Lys  Glu
     210                      215                 220
Gly  Ser  Cys  Leu  Leu  Ala  Asp  Asp  Asn  Phe  Val  Leu  Ile  Gly  Ser  Phe
225                      230                 235                           240
Val  Ser  Phe  Phe  Ile  Pro  Leu  Thr  Ile  Met  Val  Ile  Thr  Tyr  Phe  Leu
               245                 250                      255
Thr  Ile  Lys  Ser  Leu  Gln  Lys  Glu  Ala  Thr  Leu  Cys  Val  Ser  Asp  Leu
               260                 265                      270
Gly  Thr  Arg  Ala  Lys  Leu  Ala  Ser  Phe  Ser  Phe  Leu  Pro  Gln  Ser  Ser
          275                 280                 285
Leu  Ser  Ser  Glu  Lys  Leu  Phe  Gln  Arg  Ser  Ile  His  Arg  Glu  Pro  Gly
     290                 295                 300
Ser  Tyr  Thr  Gly  Arg  Arg  Thr  Met  Gln  Ser  Ile  Ser  Asn  Glu  Gln  Lys
305                 310                 315                           320
Ala  Cys  Lys  Val  Leu  Gly  Ile  Val  Phe  Phe  Leu  Phe  Val  Val  Met  Trp
               325                 330                      335
Cys  Pro  Phe  Phe  Ile  Thr  Asn  Ile  Met  Ala  Val  Ile  Cys  Lys  Glu  Ser
               340                 345                 350
Cys  Asn  Glu  Asp  Val  Ile  Gly  Ala  Leu  Leu  Asn  Val  Phe  Val  Trp  Ile
     355                 360                      365
Gly  Tyr  Leu  Ser  Ser  Ala  Val  Asn  Pro  Leu  Val  Tyr  Thr  Leu  Phe  Asn
     370                 375                      380
Lys  Thr  Tyr  Arg  Ser  Ala  Phe  Ser  Arg  Tyr  Ile  Gln  Cys  Gln  Tyr  Lys
385                      390                 395                           400
Glu  Asn  Lys  Lys  Pro  Leu  Gln  Leu  Ile  Leu  Val  Asn  Thr  Ile  Pro  Ala
               405                 410                      415
Leu  Ala  Tyr  Lys  Ser  Ser  Gln  Leu  Gln  Met  Gly  Gln  Lys  Lys  Asn  Ser
               420                 425                 430
Lys  Gln  Asp  Ala  Lys  Thr  Thr  Asp  Asn  Asp  Cys  Ser  Met  Val  Ala  Leu
          435                 440                 445
Gly  Lys  Gln  His  Ser  Glu  Glu  Ala  Ser  Lys  Asp  Asn  Ser  Asp  Gly  Val
     450                 455                 460
```

Asn Glu Lys Val Ser Cys Val
465                     470

( 2 ) INFORMATION FOR SEQ ID NO:8:

( i ) SEQUENCE CHARACTERISTICS:
         ( A ) LENGTH: 42 base pairs
         ( B ) TYPE: nucleic acid
         ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
         ( A ) ORGANISM: oligonucleotide ( x i ) SEQUENCE DESCRIPTION: SEQ ID NO:8:

GATGGTACAC TGGCTGGGGG GTGGGCTGAG TTGACGGTGG CT                        42

( 2 ) INFORMATION FOR SEQ ID NO:9:

( i ) SEQUENCE CHARACTERISTICS:
         ( A ) LENGTH: 26 base pairs
         ( B ) TYPE: nucleic acid
         ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
         ( A ) ORGANISM: oligonucleotide ( x i ) SEQUENCE DESCRIPTION: SEQ ID NO:9:

TACCACGCGG CCAAGAGCCT TTACCA                                          26

( 2 ) INFORMATION FOR SEQ ID NO:10:

( i ) SEQUENCE CHARACTERISTICS:
         ( A ) LENGTH: 25 base pairs
         ( B ) TYPE: nucleic acid
         ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
         ( A ) ORGANISM: oligonucleotide ( x i ) SEQUENCE DESCRIPTION: SEQ ID NO:10:

TGGTGCTAGA GATCTGCTGA CGTTC                                           25

( 2 ) INFORMATION FOR SEQ ID NO:11:

( i ) SEQUENCE CHARACTERISTICS:
         ( A ) LENGTH: 45 base pairs
         ( B ) TYPE: nucleic acid
         ( C ) STRANDEDNESS: single
         ( D ) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: oligonucleotide (xi) SEQUENCE DESCRIPTION: SEQ ID NO:11:

GAGAAGTCAG ACACACAGAA AGTCTGTGTA AGTTTTACAA CTTGC    45

(2) INFORMATION FOR SEQ ID NO:12:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: OLIGONUCLEOTIDE (xi) SEQUENCE DESCRIPTION: SEQ ID NO:12:

GATGGTACAC TGGCTGGGGG GTGGGCTGAG TTGACGGTGG CT    42

DNA ENCODING A HUMAN 5-HT$_{1E}$ RECEPTOR AND USES THEREOF

This is a continuation of U.S. application Ser. No. 08/194,113, filed Feb. 8, 1994, abandoned which is a continuation of U.S. application Ser. No. 07/803,626, field Dec. 2, 1991, abandoned the contents of which are hereby incorporated by reference.

BACKGROUND OF THE INVENTION

Since the purification of a pressor substance in blood serum termed serotonin (Rapport et al., 1947) and later identified as 5-hydroxytryptamine (5-HT)(Rapport, 1949), there has been a plethora of reports demonstrating that this indoleamine not only plays a role in the functioning of peripheral tissues but, indeed, performs a key role in the brain as a neurotransmitter. Certainly, the anatomical localization of serotonin and serotonergic neurons in both the peripheral and central nervous systems supports its role in such diverse physiologic and behavioral functions as pain perception, sleep, aggression, sexual activity, hormone secretion, thermoregulation, motor activity, cardiovascular function, food intake and renal regulation (For review see Green, 1985; Osborne and Hamon, 1988; Sanders-Bush, 1988; Peroutka, 1991). Taken together, it appears that serotonin plays an important role in homeostasis and in modulating responsiveness to environmental stimuli. Accordingly, studies demonstrating that abnormalities in the serotonergic system may be associated with disease states has created a drug development effort towards agents which may selectively modulate the function of serotonin (Glennon, 1990).

In relation to the characterization of physiologic or biochemical responses resulting from the release of serotonin are simultaneous investigations examining the receptor sites responsible for the actions elicited by the indoleamine transmitter. Following early in vitro pharmacological assays describing the existence of two different serotonin receptors, designated as D and M, in the guinea pig ileum (Gaddum and Picarelli, 1957), the advent of receptor binding technique in the 1970's has brought to light during the last decade the diversity of 5-HT receptors existing in both the brain and peripheral tissues. Thus, although the concept of D and M receptors has not been invalidated, serotonin receptors not fitting either category have been identified using radioligand methods. To date using this technique, there appears to be four classes of serotonin receptors found in the brain: 5-HT$_1$, 5-HT$_2$, 5-HT$_3$ and, 5-HT$_4$ (Peroutka, 1991). Furthermore, 5-HT1 sites have been subclassified as: 5-HT$_{1A}$, 5-HT$_{1B}$, 5-HT$_{1C}$, 5-HT$_{1D}$ (Hamon et al., 1990) and 5-HT$_{1E}$ (Leonhardt et al., 1989). Although a detailed characterization of the 5-HT$_{1E}$ binding site is lacking, extensive pharmacologic, biochemical and functional properties have clearly shown that the other four subtypes of 5-HT$_1$ sites are receptors according to classical criteria. Interestingly, the 5-HT$_{1E}$ binding site was first observed in human cortical tissue using [$^3$H]5-HT as the radioligand probe in the presence of 5-carboxyamidotryptamine and mesulergine to mask other members of the 5-HT$_{1E}$ receptor class. The affinity constants of the nine drugs tested indicated a unique pharmacological profile. In particular, the low affinity of 5-CT and ergotamine seemed to clearly discriminate the pharmacologically defined 5-HT$_{1D}$ site from that of this novel serotonergic site. Importantly, it was demonstrated that 5-HT$_{1E}$-sites are saturable and exist in a density consistent with other known neurotransmitter receptors. Furthermore, this site appeared to interact with a GTP-binding protein. Overall, the data provided a framework suggesting that the 5-HT$_{1E}$ binding site may represent a functional receptor.

During the last few years, the field of molecular biology has provided an important facet to receptor research by cloning these proteins and allowing more precise characterizations in isolated systems (Hartig et al., 1990). This has been accomplished for the 5-HT$_{1A}$ (Fargin et al., 1988), 5-HT$_{1C}$ (Julius et al., 1988), 5-HT$_{1D}$ (Branchek et al., 1990) and 5-HT$_2$ receptors (Pritchett et al., 1988). Thus, there is no doubt that these binding sites represent "true" functional receptors. Indeed, the pharmacological characterization of serotonin receptors involved in various physiological or biochemical functions is a key component of drug development for the serotonergic system. As one can deduce from the diversity of serotonin binding sites, many targets are available for advancement in selective drug design. The coupling of molecular biological methods to pharmacological characterization particularly for cloned human receptors will open new avenues for pharmaceutical development which have not been previously explored.

SUMMARY OF THE INVENTION

This invention provides an isolated nucleic acid molecule encoding a human 5-HT$_{1E}$ receptor.

This invention also provides an isolated protein which is a human 5-HT$_{1E}$ receptor.

This invention provides a vector comprising an isolated nucleic acid molecule encoding a human 5-HT$_{1E}$ receptor.

This invention also provides vectors such as plasmids comprising a DNA molecule encoding a human 5-HT$_{1E}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding the 5-HT$_{1E}$ receptor as to permit expression thereof.

This invention provides a mammalian cell comprising a DNA molecule encoding a human 5-HT$_{1E}$ receptor.

This invention provides a method for determining whether a ligand not known to be capable of binding to a human 5-HT$_{1E}$ receptor can bind to a human 5-HT$_{1E}$ receptor which comprises contacting a mammalian cell comprising an isolated DNA molecule encoding a human 5-HT$_{1E}$ receptor with the ligand under conditions permitting binding of ligands known to bind to a 5-HT$_{1E}$ receptor, detecting the presence of any of the ligand bound to a human 5-HT$_{1E}$ receptor, and thereby determining whether the ligand binds to a human 5-HT$_{1E}$ receptor.

This invention also provides a method for determining whether a ligand not known to be capable of binding to the human 5-HT$_{1E}$ receptor can functionally activate its activity or prevent the action of a ligand which does so. This comprises contacting a mammalian cell comprising an isolated DNA molecule which encodes a human 5-HT$_{1E}$ receptor with the ligand under conditions permitting the activation or blockade of a functional response, detected by means of a bioassay from the mammalian cell such as a second messenger response, and thereby determining whether the ligand activates or prevents the activation of the human 5-HT$_{1E}$ receptor functional output.

This invention further provides a method of screening drugs to identify drugs which specifically interact with, and bind to, the human 5-HT$_{1E}$ receptor on the surface of a cell which comprises contacting a mammalian cell comprising an isolated DNA molecule encoding a human 5-HT$_{1E}$ receptor with a plurality of drugs, determining those drugs which bind to the mammalian cell, and thereby identifying drugs which specifically interact with, and bind to, a human $5\text{-HT}_{1E}$ receptor.

This invention also provides a method of screening drugs to identify drugs which interact with, and activate or block the activation of, the human $5\text{-HT}_{1E}$ receptor on the surface of a cell which comprises contacting the mammalian cell comprising an isolated DNA molecule encoding and expressing a human $5\text{-HT}_{1E}$ receptor with a plurality of drugs, determining those drugs which activate or block the activation of the receptor in the mammalian cell using a bioassay such as a second messenger assays, and thereby identifying drugs which specifically interact with, and activate or block the activation of, a human $5\text{-HT}_{1E}$ receptor.

This invention provides a nucleic acid probe comprising a nucleic acid molecule of at least 15 nucleotides capable of specifically hybridizing with a sequence included within the sequence of a nucleic acid molecule encoding a human $5\text{-HT}_{1E}$ receptor.

This invention also provides a method of detecting expression of the $5\text{-HT}_{1E}$ receptor on the surface of a cell by detecting the presence of mRNA coding for a $5\text{-HT}_{1E}$ receptor which comprises obtaining total mRNA from the cell and contacting the mRNA so obtained with a nucleic acid probe comprising a nucleic acid molecule of at least 15 nucleotides capable of specifically hybridizing with a sequence included within the sequence of a nucleic acid molecule encoding a human $5\text{-HT}_{1E}$ receptor under hybridizing conditions, detecting the presence of mRNA hybridized to the probe, and thereby detecting the expression of the $5\text{-HT}_{1E}$ receptor by the cell.

This invention provides an antisense oligonucleotide having a sequence capable of binding specifically with any sequences of an mRNA molecule which encodes a human $5\text{-HT}_{1E}$ receptor so as to prevent translation of the mRNA molecule.

This invention provides an antibody directed to a human $5\text{-HT}_{1E}$ receptor.

This invention provides a transgenic nonhuman mammal expressing DNA encoding a human $5\text{-HT}_{1E}$ receptor. This invention also provides a transgenic nonhuman mammal expressing DNA encoding a human $5\text{-HT}_{1E}$ receptor so mutated as to be incapable of normal receptor activity, and not expressing native $5\text{-HT}_{1E}$ receptor. This invention further provides a transgenic nonhuman mammal whose genome comprises antisense DNA complementary to DNA encoding a human $5\text{-HT}_{1E}$ receptor so placed as to be transcribed into antisense mRNA which is complementary to mRNA encoding a $5\text{-HT}_{1E}$ receptor and which hybridizes to mRNA encoding a $5\text{-HT}_{1E}$ receptor thereby reducing its translation.

This invention provides a method of determining the physiological effects of expressing varying levels of human $5\text{-HT}_{1E}$ receptors which comprises producing a transgenic nonhuman animal whose levels of human $5\text{-HT}_{1E}$ receptor expression are varied by use of an inducible promoter which regulates human $5\text{-HT}_{1E}$ receptor expression.

This invention also provides a method of determining the physiological effects of expressing varying levels of human $5\text{-HT}_{1E}$ receptors which comprises producing a panel of transgenic nonhuman animals each expressing a different amount of human $5\text{-HT}_{1E}$ receptor.

This invention provides a method for diagnosing a predisposition to a disorder associated with the expression of a specific human $5\text{-HT}_{1E}$ receptor allele which comprises: a. obtaining DNA of subjects suffering from the disorder: b. performing a restriction digest of the DNA with a panel of restriction enzymes; c. electrophoretically separating the resulting DNA fragments on a sizing gel; d. contacting the resulting gel with a nucleic acid probe capable of specifically hybridizing to DNA encoding a human $5\text{-HT}_{1E}$ receptor and labelled with a detectable marker; e. detecting labelled bands which have hybridized to the DNA encoding a human $5\text{-HT}_{1E}$ receptor labelled with a detectable marker to create a unique band pattern specific to the DNA of subjects suffering from the disorder; f. preparing DNA obtained for diagnosis by steps a–e; and g. comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method of preparing the isolated $5\text{-HT}_{1E}$ receptor which comprises inducing cells to express $5\text{-HT}_{1E}$ receptor, recovering the receptor from the resulting cells and purifying the receptor so recovered.

This invention also provides a method of preparing the isolated $5\text{-HT}_{1E}$ receptor which comprises inserting nucleic acid encoding $5\text{-HT}_{1E}$ receptor in a suitable vector, inserting the resulting vector in a suitable host cell, recovering the receptor produced by the resulting cell, and purifying the receptor so recovered.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention also provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides a transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

BRIEF DESCRIPTION OF THE FIGURES

FIG. 1. Nucleotide and deduced amino acid sequence of gene $5\text{-HT}_{1E}$. (Seq. I.D. Nos. 1 and 2).

Numbers above the nucleotide sequence indicate nucleotide position. DNA sequence was determined by the chain termination method of Sanger, et al., on denatured double-stranded plasmid templates using the enzyme Sequenase. Deduced amino acid sequence (single letter code) of a long open reading frame is shown.

FIG. 2. Comparison of the human 5-HT$_{1E}$ receptor primary structures with other serotonin receptors. (Seq. I.D. Nos. 3 - 5HT$_{1A}$; 4- 5HT$_{1C}$; 5- 5HT$_{1D\alpha}$; 6- 5HT$_{1D\beta}$; 7- 5HT$_2$)

Amino acid sequences (single letter code) are aligned to optimize homology. The putative transmembrane spanning domains are indicated by stars and identified by Roman numerals (TM I–VII).

Figure 3:
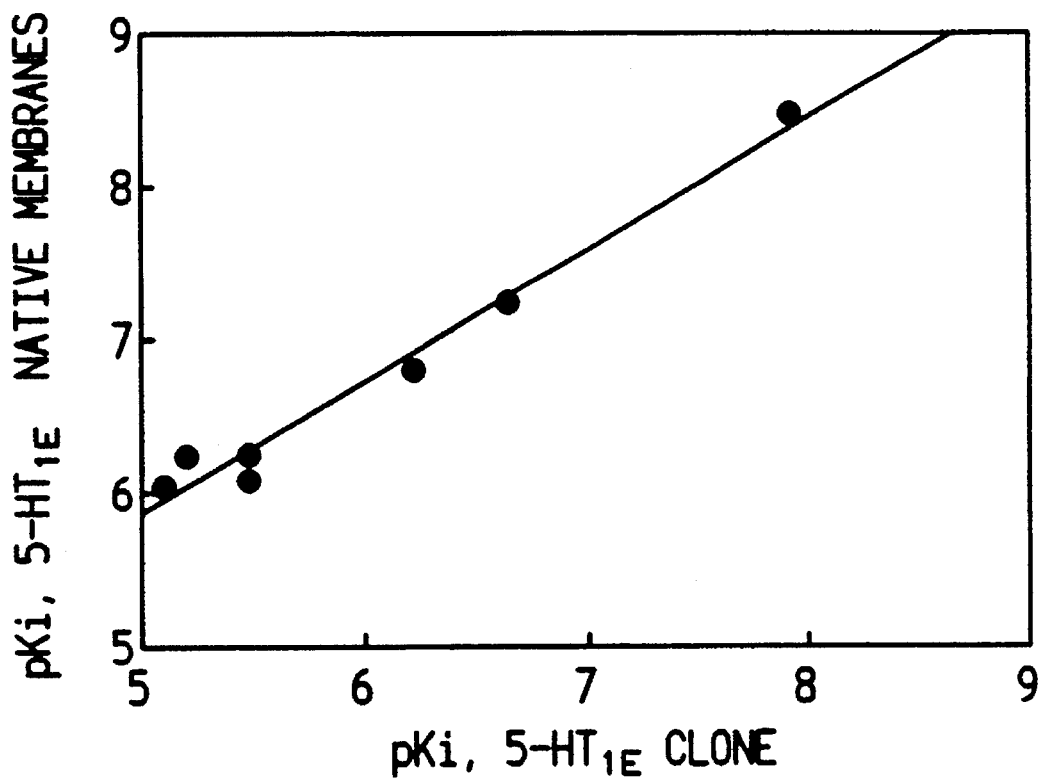

FIG. 3. Respective pKi values of various drugs for the inhibition of [$^3$H]5-HT specific binding to the cloned 5-HT$_{1E}$ receptor and human cortical membrane preparations containing the native 5-HT$_{1E}$ receptor.

Values for the native membrane preparation are taken from Leonhardt et al., 1989. "r" is the correlation coefficient between pKi values calculated for the two receptor preparations and clearly indicates the similarity in binding profile.

Figure 4:
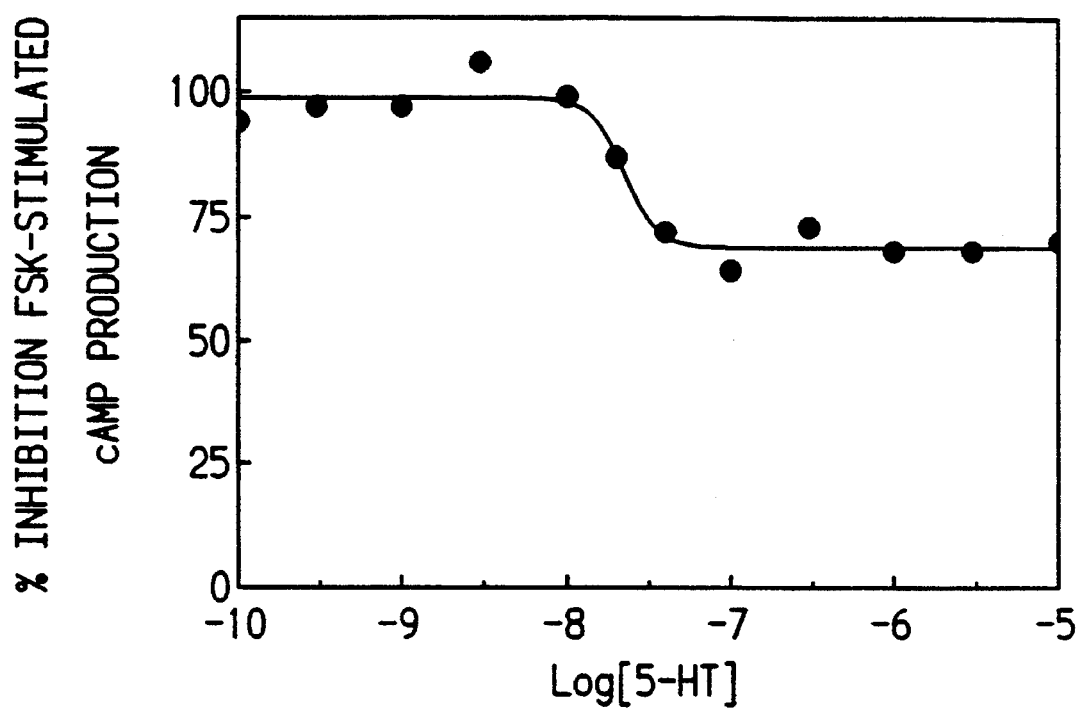

FIG. 4. 5-HT concentration-effect curve for the inhibition of forskolin-stimulated CAMP formation in Y1 cells transfected with the 5-HT$_{1E}$ receptor.

Values are expressed as a percentage of forskolin(Fsk)-stimulated cAMP production.

FIG. 5. 5-HT$_{1E}$ mRNA localization in the human brain.

cDNA was reverse transcribed from total RNA (5 µg) using random hexamers (500 pmoles). One microgram of cDNA was subjected to 30 cycles of PCR amplification using 5'- and 3'-primers directed to the third cytoplasmic loop of the 5HT1E receptor gene. Amplified fragments were subjected to Southern blot analysis using an end-labeled oligonucleotide probe which was internal to the PCR primers. (+) control consisted of 5HT1E recombinant plasmid; (−) control consisted of all cDNA and PCR reagents without the addition of cDNA template. Intensity of signal is depicted as the number of plus signs as defined in the figure key.

DETAILED DESCRIPTION OF THE INVENTION

As used herein, the 5-HT receptor family is defined as the group of mammalian proteins that function as receptors for serotonin. A 5-HT receptor subfamily is defined as a subset of proteins belonging to the 5-HT receptor family which are encoded by genes which exhibit homology of greater than 72% or higher with each other in their deduced amino acid sequences within presumed transmembrane regions (linearly contiguous stretches of hydrophobic amino acids, bordered by charged or polar amino acids, that are long enough to form secondary protein structures that span a lipid bilayer). Four human 5-HT receptor subfamilies can be distinguished based on the information presently available: 5-HT$_1$, 5-HT$_2$, 5-HT$_3$, and 5-HT$_4$ (Peroutka, 1991). The 5-HT$_2$ receptor subfamily contains the human 5-HT$_2$ receptor. Although no other human members of this family have been described, the rat 5-HT$_2$ receptor (Pritchett, et al. 1988; Julius, et al. Proc. Natl. Acad. Sci. USA 87:928–932, 1990) and the rat 5HT$_{1C}$ receptor (Julius, et al. 1988) constitute a rat 5-HT receptor subfamily. The 5-HT$_1$ subfamily has been subdivided further as: 5-HT$_{1A}$, 5-HT$_{1B}$, 5-HT$_{1C}$, 5-HT$_{1D}$ (Hamon et al., 1990) and 5-HT$_{1E}$ (Leonhardt et al., 1989). The 5-HT$_{1A}$ subfamily contains the human 5-HT$_{1A}$ receptor, also known as G-21 (Fargin, et al. 1988) The 5-HT$_{1D}$ receptor subfamily contains two members, the 5-HT$_{1D-1}$ receptor (also termed 5-HT$_{1D\alpha}$) and the 5-HT$_{1D-2}$ receptor (also termed 5-HT$_{1D\beta}$). The 5-HT$_{1E}$ subfamily contains the human 5-HT$_{1E}$ receptor (also termed clone hp75d). Although this definition differs from the pharmacological definition used earlier, there is significant overlap between the present definition and the pharmacological definition. Members of the 5-HT$_{1E}$ receptor subfamily so described include the 5-HT$_{1E}$ receptor and any other receptors which have a greater than 72% homology to the DNA and amino acid sequence shown in FIG. 1 according to the definition of "subfamily". This invention relates to the discovery of the first member of the human 5-HT$_{1E}$ receptor subfamily.

This invention provides an isolated nucleic acid molecule encoding a human 5-HT$_{1E}$ receptor. As used herein, the term "isolated nucleic acid molecule" means a nucleic acid molecule that is, a molecule in a form which does not occur in nature. Such a receptor is by definition a member of the 5-HT$_{1E}$ receptor subfamily. Therefore, any receptor which meets the defining criteria given above is a human 5-HT$_{1E}$ receptor. One means of isolating a human 5-HT$_{1E}$ receptor is to probe a human genomic library with a natural or artificially designed DNA probe, using methods well known in the art. DNA probes derived from the human receptor gene 5-HT$_{1E}$ are particularly useful probes for this purpose. DNA and cDNA molecules which encode human 5-HT$_{1E}$ receptors may be used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule encoding a human 5-HT$_{1E}$ receptor. Such molecules may have coding sequences substantially the same as the coding sequence shown in FIG. 1. The DNA molecule of FIG. 1 encodes the sequence of the human 5-HT$_{1E}$ receptor gene.

This invention further provides a cDNA molecule of encoding a human 5-HT$_{1E}$ receptor having a coding sequence substantially the same as the coding sequence shown in FIG. 1. This molecule is obtained by the means described above.

This invention also provides an isolated protein which is a human 5-HT$_{1E}$ receptor. As used herein, the term "isolated protein means a protein molecule free of other cellular components. An example of such protein is an isolated protein having substantially the same amino acid sequence as the amino acid sequence shown in FIG. 1 which is a human 5-HT$_{1E}$ receptor. One means for obtaining isolated 5-HT$_{1E}$ receptor is to express DNA encoding the receptor in a suitable host, such as a bacterial, yeast, or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising an isolated nucleic acid molecule such as DNA, RNA, or cDNA encoding a human 5-HT$_{1E}$ receptor. Examples of vectors are viruses such as bacteriophages (such as phage lambda), cosmids, plasmids (such as pUC18, available from Pharmacia, Piscataway, N.J.), and other recombination vectors.

Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. A specific example of such plasmids is a plasmid comprising cDNA having a coding sequence substantially the same as the coding sequence shown in FIG. 1 and designated clone hp75d (Seq. I.D. No. 1).

This invention also provides vectors comprising a DNA molecule encoding a human $5\text{-HT}_{1E}$ receptor, adapted for expression in a bacterial cell, a yeast cell, or a mammalian cell which additionally comprise the regulatory elements necessary for expression of the DNA in the bacterial, yeast, or mammalian cells so located relative to the DNA encoding a human $5\text{-HT}_{1E}$ receptor as to permit expression thereof. DNA having coding sequences substantially the same as the coding sequence shown in FIG. 1 may usefully be inserted into the vectors to express human $5\text{-HT}_{1E}$ receptors. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial, yeast, or, in particular, a mammalian cell which comprises a DNA molecule encoding a human $5\text{-HT}_{1E}$ receptor and the regulatory elements necessary for expression of the DNA in the bacterial, yeast, or mammalian cell so located relative to the DNA encoding a human $5\text{-HT}_{1E}$ receptor as to permit expression thereof. Some plasmids adapted for expression in a mammalian cell are pSVL (available from Pharmacia, Piscataway, N.J.) and pcEXV-3 (Miller J. and Germain R. N., J. Exp. Med. 164:1478 (1986)). A specific example of such plasmid is a plasmid adapted for expression in a mammalian cell comprising cDNA having coding sequences substantially the same as the coding sequence shown in FIG. 1 and the regulatory elements necessary for expression of the DNA in the mammalian cell which is designated pcEXV-hp75d and deposited under ATCC Accession No. 75138. Those skilled in the art will readily appreciate that numerous plasmids adapted for expression in a mammalian cell which comprise DNA of encoding human $5\text{-HT}_{1E}$ receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposit discussed supra, and the other deposits discussed herein, were made pursuant to, and in satisfaction of, the Budapest Treaty on the International Recognition of the Deposit of Microorganisms for the Purpose of Patent Procedure with the American Type Culture Collection (ATCC), 12301 Parklawn Drive, Rockville, Md. 20852. The deposit of stains bearing accession numbers ATCC 75138, CRL 10913 and CRL 10914 were so made Nov. 6, 1991.

This invention provides a mammalian cell comprising a DNA molecule encoding a human $5\text{-HT}_{1E}$ receptor, such as a mammalian cell comprising a plasmid adapted for expression in a mammalian cell, which comprises a DNA molecule encoding a human $5\text{-HT}_{1E}$ receptor, the protein encoded thereby is expressed on the cell surface, and the regulatory elements necessary for expression of the DNA in the mammalian cell so located relative to the DNA encoding a human $5\text{-HT}_{1E}$ receptor as to permit expression thereof. Numerous mammalian cells may be used as hosts, including, for example, the mouse fibroblast cell NIH3T3, CHO cells, HeLa cells, Ltk$^-$ cells, Y1 cells, etc. A particular example of an Ltk$^-$ cell is a cell designated $5\text{-HT}_{1E}\text{-}7$ and deposited under ATCC Accession No. CRL 10913 and comprises the plasmid designated pcEXV-hp75d. Another example is the murine adrenal Y1 cell line designated Y-5-HT$_{1E}$ and deposited under ATCC Accession No. CRL 10914. Expression plasmids such as that described supra may be used to transfect mammalian cells by methods well known in the art such as calcium phosphate precipitation, or DNA encoding these $5\text{-HT}_{1E}$ receptors may be otherwise introduced into mammalian cells, e.g., by microinjection, to obtain mammalian cells which comprise DNA, e.g., cDNA or a plasmid, encoding either human $5\text{-HT}_{1E}$ receptor.

This invention provides a method for determining whether a ligand not known to be capable of binding to a human $5\text{-HT}_{1E}$ receptor can bind to a human $5\text{-HT}_{1E}$ receptor which comprises contacting a mammalian cell comprising a DNA molecule encoding a human $5\text{-HT}_{1E}$ receptor, the protein encoded thereby is expressed on the cell surface, with the ligand under conditions permitting binding of ligands known to bind to the $5\text{-HT}_{1E}$ receptor, detecting the presence of any of the ligand bound to the $5\text{-HT}_{1E}$ receptor, and thereby determining whether the ligand binds to the $5\text{-HT}_{1E}$ receptor. This invention also provides a method for determining whether a ligand not known to be capable of binding to the human $5\text{-HT}_{1E}$ receptor can functionally activate its activity or prevent the action of a ligand which does so. This comprises contacting a mammalian cell comprising an isolated DNA molecule which encodes a human $5\text{-HT}_{1E}$ receptor with the ligand under conditions permitting the activation or blockade of a functional response, detected by means of a bioassay from the mammalian cell such as a second messenger response, and thereby determining whether the ligand activates or prevents the activation of the human $5\text{-HT}_{1E}$ receptor functional output. The DNA in the cell may have a coding sequence substantially the same as the coding sequence shown in FIG. 1 preferably, the mammalian cell is nonneuronal in origin. An example of a nonneuronal mammalian cell is an Ltk$^-$ cell, in particular the Ltk$^-$ cell designated $5\text{-HT}_{1E}\text{-}7$. Another example of a nonneuronal mammalian cell to be used for functional assays is a Y1 murine adrenal cell, specifically the Y1 cell designated Y-5-HT$_{1E}$. The preferred method for determining whether a ligand is capable of binding to the human $5\text{-HT}_{1E}$ receptor comprises contacting a transfected nonneuronal mammalian cell (i.e. a cell that does not naturally express any type of 5-HT or G-protein coupled receptor, thus will only express such a receptor if it is transfected into the cell) expressing a 5-HT$_{1E}$ receptor on its surface, or contacting a membrane preparation derived from such a transfected cell, with the ligand under conditions which are known to prevail, and thus to be associated with, in vivo binding of the ligands to a 5-HT$_{1E}$ receptor, detecting the presence of any of the ligand being tested bound to the 5-HT$_{1E}$ receptor on the surface of the cell, and thereby determining whether the ligand binds to, activates or prevents the activation of the 5-HT$_{1E}$ receptor. This response system is obtained by transfection of isolated DNA into a suitable host cell containing the desired second messenger system such as phosphoinositide hydrolysis, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human 5-HT$_{1E}$ receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human 5-HT$_{1E}$ receptor. The transfection system is also useful for determining the affinity and efficacy of known drugs at the human 5-HT$_{1E}$ receptor sites.

This invention also provides a method of screening drugs to identify drugs which specifically interact with, and bind to, the human 5-HT$_{1E}$ receptor on the surface of a cell which comprises contacting a mammalian cell comprising a DNA molecule encoding a human 5-HT$_{1E}$ receptor on the surface of a cell with a plurality of drugs, determining those drugs which bind to the mammalian cell, and thereby identifying drugs which specifically interact with, and bind to, the human 5-HT$_{1E}$ receptor. This invention also provides a method of screening drugs to identify drugs which interact with, and activate or block the activation of, the human 5-HT$_{1E}$ receptor on the surface of a cell which comprises contacting the mammalian cell comprising an isolated DNA molecule encoding and expressing a human 5-HT$_{1E}$ receptor with a plurality of drugs, determining those drugs which activate or block the activation of the receptor in the mammalian cell using a bioassay such as a second messenger assays, and thereby identifying drugs which specifically interact with, and activate or block the activation of, a human 5-HT$_{1E}$ receptor. The DNA in the cell may have a coding sequence substantially the same as the coding sequence shown in FIG. 1. Preferably, the mammalian cell is nonneuronal in origin. An example of a nonneuronal mammalian cell is an Ltk$^-$ cell, in particular the Ltk$^-$ cell designated 5-HT$_{1E}$-7. Another example of a non-neuronal mammalian cell to be used for functional assays is a Y1 murine adrenal cell, specifically the Y1 cell designated Y-5-HT$_{1E}$. Drug candidates are identified by choosing chemical compounds which bind with high affinity to the expressed 5-HT$_{1E}$ receptor protein in transfected cells, using radioligand binding methods well known in the art, examples of which are shown in the binding assays described herein. Drug candidates are also screened for selectivity by identifying compounds which bind with high affinity to one particular 5-HT$_{1E}$ receptor subtype but do not bind with high affinity to any other serotonin receptor subtype or to any other known receptor site. Because selective, high affinity compounds interact primarily with the target 5-HT$_{1E}$ receptor site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention provides a nucleic acid probe comprising a nucleic acid molecule of at least 15 nucleotides capable of specifically hybridizing with a sequence included within the sequence of a nucleic acid molecule encoding a human 5-HT$_{1E}$ receptor, for example with a coding sequence included within the sequence shown in FIG. 1. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding human 5-HT$_{1E}$ receptors is useful as a diagnostic test for any disease process in which levels of expression of the corresponding 5-HT$_{1E}$ receptor is altered. DNA probe molecules are produced by insertion of a DNA molecule which encodes human 5-HT$_{1E}$ receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. An example of such DNA molecule is shown in FIG. 1. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes human 5-HT$_{1E}$ receptor of are useful as probes for these genes, for their associated mRNA, or for the isolation of related genes by homology screening of genomic or cDNA libraries, or by the use of amplification techniques such as the Polymerase Chain Reaction. Synthesized oligonucleotides as described may also be used to determine the cellular localization of the mRNA produced by the 5-$HT_{1E}$ gene by in situ hybridization. An example of such an oligonucleotide is: GATGGTACACTG-GCTGGGGGGTGGGCTGAGTTGACGGTGGCT(Seq. I.D. No. 8).

This invention also provides a method of detecting expression of a 5-$HT_{1E}$ receptor on the surface of a cell by detecting the presence of mRNA coding for a 5-$HT_{1E}$ receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding a human 5-$HT_{1E}$ receptor under hybridizing conditions, detecting the presence of mRNA hybridized to the probe, and thereby detecting the expression of the 5-$HT_{1E}$ receptor by the cell. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a human 5-$HT_{1E}$ receptor so as to prevent translation of the mRNA molecule. The antisense oligonucleotide may have a sequence capable of binding specifically with any sequences of the cDNA molecule whose sequence is shown in FIG. 1. As used herein, the phrase "binding specifically" means the ability of a nucleic acid sequence to recognize a nucleic acid sequence complementary to its own and to form double-helical segments through hydrogen bonding between complementary base pairs. A particular example of an antisense oligonucleotide is an antisense oligonucleotide comprising chemical analogues of nucleotides.

This invention also provides a pharmaceutical composition comprising an amount of the oligonucleotide described above effective to reduce expression of a human 5-$HT_{1E}$ receptor by passing through a cell membrane and binding specifically with mRNA encoding a human 5-$HT_{1E}$ receptor in the cell so as to prevent its translation and a pharmaceutically acceptable hydrophobic carrier capable of passing through a cell membrane. The oligonucleotide may be coupled to a substance which inactivates mRNA, such as a ribozyme. The pharmaceutically acceptable hydrophobic carrier capable of passing through cell membranes may also comprise a structure which binds to a receptor specific for a selected cell type and is thereby taken up by cells of the selected cell type. The structure may be part of a protein known to bind a cell-type specific receptor, for example an insulin molecule, which would target pancreatic cells. DNA molecules having coding sequences substantially the same as the coding sequence shown in FIG. 1 may be used as the oligonucleotides of the pharmaceutical composition.

This invention also provides a method of treating abnormalities which are alleviated by reduction of expression of a 5-$HT_{1E}$ receptor which comprises administering to a subject an amount of the pharmaceutical composition described above effective to reduce expression of the 5-$HT_{1E}$ receptor by the subject. This invention further provides a method of treating an abnormal condition related to 5-$HT_{1E}$ receptor activity which comprises administering to a subject an amount of the pharmaceutical composition described above effective to reduce expression of the 5-$HT_{1E}$ receptor by the subject. Several examples of such abnormal conditions are dementia, Parkinson's disease, feeding disorders, pathological anxiety, schizophrenia, or a migraine headache.

Antisense oligonucleotide drugs inhibit translation of mRNA encoding these receptors. Synthetic oligonucleotides, or other antisense chemical structures are designed to bind to mRNA encoding the 5-$HT_{1E}$ receptor and inhibit translation of mRNA and are useful as drugs to inhibit expression of 5-$HT_{1E}$ receptor genes in patients. This invention provides a means to therapeutically alter levels of expression of human 5-$HT_{1E}$ receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIG. 1 of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequence shown in FIG. 1 by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of $5\text{-}HT_{1E}$ receptors.

This invention provides an antibody directed to the human $5\text{-}HT_{1E}$ receptor, for example a monoclonal antibody directed to an epitope of a human $5\text{-}HT_{1E}$ receptor present on the surface of a cell and having an amino acid sequence substantially the same as an amino acid sequence for a cell surface epitope of the human $5\text{-}HT_{1E}$ receptor included in the amino acid sequence shown in FIG. 1 (Seq. I.D. No. 2). Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIG. 1 will bind to a surface epitope of a human $5\text{-}HT_{1E}$ receptor, as described. Antibodies directed to human $5\text{-}HT_{1E}$ receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk$^-$ cells may be used as immunogens to raise such an antibody. Alternatively, synthetic peptides may be prepared using commercially available machines and the amino acid sequence shown in FIG. 1 (Seq. I.D. No. 2). As a still further alternative, DNA, such as a cDNA or a fragment thereof, may be cloned and expressed and the resulting polypeptide recovered and used as an immunogen. These antibodies are useful to detect the presence of human $5\text{-}HT_{1E}$ receptors encoded by the isolated DNA, or to inhibit the function of the receptors in living animals, in humans, or in biological tissues or fluids isolated from animals or humans.

This invention provides a pharmaceutical composition which comprises an amount of an antibody directed to the human $5\text{-}HT_{1E}$ receptor effective to block binding of naturally occurring ligands to the $5\text{-}HT_{1E}$ receptor, and a pharmaceutically acceptable carrier. A monoclonal antibody directed to an epitope of a human $5\text{-}HT_{1E}$ receptor present on the surface of a cell and having an amino acid sequence substantially the same as an amino acid sequence for a cell surface epitope of the human $5\text{-}HT_{1E}$ receptor included in the amino acid sequence shown in FIG. 1 is useful for this purpose.

This invention also provides a method of treating abnormalities which are alleviated by reduction of expression of a human $5\text{-}HT_{1E}$ receptor which comprises administering to a subject an amount of the pharmaceutical composition described above effective to block binding of naturally occurring ligands to the $5\text{-}HT_{1E}$ receptor and thereby alleviate abnormalities resulting from overexpression of a human $5\text{-}HT_{1E}$ receptor. Binding of the antibody to the receptor prevents the receptor from functioning, thereby neutralizing the effects of overexpression. The monoclonal antibodies described above are both useful for this purpose. This invention additionally provides a method of treating an abnormal condition related to an excess of $5\text{-}HT_{1E}$ receptor activity which comprises administering to a subject an amount of the pharmaceutical composition described above effective to block binding of naturally occurring ligands to the $5\text{-}HT_{1E}$ receptor and thereby alleviate the abnormal condition. Some examples of abnormal conditions are dementia, Parkinson's disease, feeding disorders, pathological anxiety, schizophrenia, and a migraine headache.

This invention provides a method of detecting the presence of a $5\text{-}HT_{1E}$ receptor on the surface of a cell which comprises contacting the cell with an antibody directed to the human $5\text{-}HT_{1E}$ receptor, under conditions permitting binding of the antibody to the receptor, detecting the presence of the antibody bound to the cell, and thereby the presence of the human $5\text{-}HT_{1E}$ receptor on the surface of the cell. Such a method is useful for determining whether a given cell is defective in expression of $5\text{-}HT_{1E}$ receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose. This invention provides a transgenic nonhuman mammal expressing DNA encoding a human $5\text{-}HT_{1E}$ receptor. This invention also provides a transgenic nonhuman mammal expressing DNA encoding a human $5\text{-}HT_{1E}$ receptor so mutated as to be incapable of normal receptor activity, and not expressing native $5\text{-}HT_{1E}$ receptor. This invention also provides a transgenic nonhuman mammal whose genome comprises antisense DNA complementary to DNA encoding a human $5\text{-}HT_{1E}$ receptor so placed as to be transcribed into antisense mRNA which is complementary to mRNA encoding a $5\text{-}HT_{1E}$ receptor and which hybridizes to mRNA encoding a $5\text{-}HT_{1E}$ receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequence shown in FIG. 1. An example of a transgenic animal is a transgenic mouse. Examples of tissue specificity-determining regions are the metallothionein promotor (Low, M. J., Lechan, R. M., Hammer, R. E. et al. Science 231:1002–1004 (1986)) and the L7 promotor (Oberdick, J., Smeyne, R. J., Mann, J. R., Jackson, S. and Morgan, J. I. Science 248:223–226 (1990)).

Animal model systems which elucidate the physiological and behavioral roles of human $5\text{-}HT_{1E}$ receptors are produced by creating transgenic animals in which the expression of a $5\text{-}HT_{1E}$ receptor is either increased or decreased, or the amino acid sequence of the expressed $5\text{-}HT_{1E}$ receptor protein is altered, by a variety of techniques. Examples of these techniques include: 1) Insertion of normal or mutant versions of DNA encoding a human $5\text{-}HT_{1E}$ receptor or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)). 2) Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these $5\text{-}HT_{1E}$ receptors. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a human $5\text{-HT}_{1E}$ receptor is purified from a vector (such as plasmid pCEXV-hp75d described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against these $5\text{-HT}_{1E}$ receptors even before such drugs become available. These animal model systems are useful for predicting or evaluating possible therapeutic applications of drugs which activate or inhibit these $5\text{-HT}_{1E}$ receptors by inducing or inhibiting expression of the native or trans-gene and thus increasing or decreasing expression of normal or mutant $5\text{-HT}_{1E}$ receptors in the living animal. Thus, a model system is produced in which the biological activity of drugs directed against these $5\text{-HT}_{1E}$ receptors are evaluated before such drugs become available. The transgenic animals which over or under produce the $5\text{-HT}_{1E}$ receptor indicate by their physiological state whether over or under production of the $5\text{-HT}_{1E}$ receptor is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which downregulates or acts as an antagonist to $5\text{-HT}_{1E}$ receptor is indicated as worth developing, and if a promising therapeutic application is uncovered by these animal model systems, activation or inhibition of the $5\text{-HT}_{1E}$ receptor is achieved therapeutically either by producing agonist or antagonist drugs directed against these $5\text{-HT}_{1E}$ receptors or by any method which increases or decreases the expression of these $5\text{-HT}_{1E}$ receptors in man.

This invention provides a method of determining the physiological effects of expressing varying levels of human $5\text{-HT}_{1E}$ receptors which comprises producing a transgenic nonhuman animal whose levels of human $5\text{-HT}_{1E}$ receptor expression are varied by use of an inducible promoter which regulates human $5\text{-HT}_{1E}$ receptor expression. This invention also provides a method of determining the physiological effects of expressing varying levels of human $5\text{-HT}_{1E}$ receptors which comprises producing a panel of transgenic nonhuman animals each expressing a different amount of human $5\text{-HT}_{1E}$ receptor. Such animals may be produced by introducing different amounts of DNA encoding a human $5\text{-HT}_{1E}$ receptor into the oocytes from which the transgenic animals are developed.

This invention also provides a method for identifying a substance capable of alleviating abnormalities resulting from overexpression of a human $5\text{-HT}_{1E}$ receptor comprising administering the substance to a transgenic nonhuman mammal expressing at least one artificially introduced DNA molecule encoding a human $5\text{-HT}_{1E}$ receptor and determining whether the substance alleviates the physical and behavioral abnormalities displayed by the transgenic nonhuman mammal as a result of overexpression of a human $5\text{-HT}_{1E}$ receptor. As used herein, the term "substance" means a compound or composition which may be natural, synthetic, or a product derived from screening. Examples of DNA molecules are DNA or cDNA molecules having a coding sequence substantially the same as the coding sequence shown in FIG. 1.

This invention provides a pharmaceutical composition comprising an amount of the substance described supra effective to alleviate the abnormalities resulting from overexpression of $5\text{-HT}_{1E}$ receptor and a pharmaceutically acceptable carrier.

This invention further provides a method for treating the abnormalities resulting from overexpression of a human $5\text{-HT}_{1E}$ receptor which comprises administering to a subject an amount of the pharmaceutical composition described above effective to alleviate the abnormalities resulting from overexpression of a human $5\text{-HT}_{1E}$ receptor.

This invention provides a method for identifying a substance capable of alleviating the abnormalities resulting from underexpression of a human $5\text{-HT}_{1E}$ receptor comprising administering the substance to the transgenic nonhuman mammal described above which expresses only nonfunctional human $5\text{-HT}_{1E}$ receptor and determining whether the substance alleviates the physical and behavioral abnormalities displayed by the transgenic nonhuman mammal as a result of underexpression of a human $5\text{-HT}_{1E}$ receptor.

This invention also provides a pharmaceutical composition comprising an amount of a substance effective to alleviate abnormalities resulting from underexpression of $5\text{-HT}_{1E}$ receptor and a pharmaceutically acceptable carrier.

This invention further provides a method for treating the abnormalities resulting from underexpression of a human $5\text{-HT}_{1E}$ receptor which comprises administering to a subject an amount of the pharmaceutical composition described above effective to alleviate the abnormalities resulting from underexpression of a human $5\text{-HT}_{1E}$ receptor.

This invention provides a method for diagnosing a predisposition to a disorder associated with the expression of a specific human 5-HT$_{1E}$ receptor allele which comprises: a) obtaining DNA of subjects suffering from the disorder: b) performing a restriction digest of the DNA with a panel of restriction enzymes; c.electrophoretically separating the resulting DNA fragments on a sizing gel: d) contacting the resulting gel with a nucleic acid probe capable of specifically hybridizing to DNA encoding a human 5-HT$_{1E}$ receptor and labelled with a detectable marker; e) detecting labelled bands which have hybridized to the DNA encoding a human 5-HT$_{1E}$ receptor label led with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human 5-HT$_{1E}$ receptor allele.

This invention provides a method of preparing the isolated 5-HT$_{1E}$ receptor which comprises inducing cells to express 5-HT$_{1E}$ receptor, recovering the receptor from the resulting cells, and purifying the receptor so recovered. An example of an isolated 5-HT$_{1E}$ receptor is an isolated protein having substantially the same amino acid sequence as the amino acid sequence shown in FIG. 1. For example, cells can be induced to express receptors by exposure to substances such as hormones. The cells can then be homogenized and the receptor isolated from the homogenate using an affinity column comprising, for example, serotonin or another substance which is known to bind to the receptor. The resulting fractions can then be purified by contacting them with an ion exchange column, and determining which fraction contains receptor activity or binds anti-receptor antibodies.

This invention provides a method of preparing the isolated 5-HT$_{1E}$ receptor which comprises inserting nucleic acid encoding 5-HT$_{1E}$ receptor in a suitable vector, inserting the resulting vector in a suitable host cell, recovering the receptor produced by the resulting cell, and purifying the receptor so recovered. An example of an isolated 5-HT$_{1E}$ receptor is an isolated protein having substantially the same amino acid sequence as the amino acid sequence shown in FIG. 1. This method for preparing 5-HT$_{1E}$ receptor uses recombinant DNA technology methods well known in the art. For example, isolated nucleic acid encoding 5-HT$_{1E}$ receptor is inserted in a suitable vector, such as an expression vector. A suitable host cell, such as a bacterial cell, or a eukaryotic cell such as a yeast cell, is transfected with the vector. 5-HT$_{1E}$ receptor is isolated from the culture medium by affinity purification or by chromatography or by other methods well known in the art.

This invention provides an antisense oligonucleotide having a sequence capable of binding specifically with any sequences of an mRNA molecule which encodes a receptor so as to prevent translation of the mRNA molecule.

This invention also provides a transgenic nonhuman mammal expressing DNA encoding a receptor.

This invention further provides a transgenic nonhuman mammal expressing DNA encoding a receptor so mutated as to be incapable of normal receptor activity, and not expressing native receptor.

This invention provides a method of determining the physiological effects of expressing varying levels of a receptor which comprises producing a transgenic nonhuman animal whose levels of receptor expression are varied by use of an inducible promoter which regulates receptor expression.

This invention also provides a method of determining the physiological effects of expressing varying levels of a receptor which comprises producing a panel of transgenic nonhuman animals each expressing a different amount of the receptor.

This invention further provides transgenic nonhuman mammal whose genome comprises antisense DNA complementary to DNA encoding a receptor so placed as to be transcribed into antisense mRNA which is complementary to mRNA encoding the receptor and which hybridizes to mRNA encoding the receptor thereby preventing its translation.

This invention provides a method for determining whether a ligand not known to be capable of binding to a receptor can bind to a receptor which comprises contacting a mammalian cell comprising an isolated DNA molecule encoding the receptor with the ligand under conditions permitting binding of ligands known to bind to a receptor, detecting the presence of any of the ligand bound to the receptor, and thereby determining whether the ligand binds to the receptor.

Applicants have identified individual receptor subtype proteins and have described methods for the identification of pharmacological compounds for therapeutic treatments. Pharmacological compounds which are directed against specific receptor subtypes provide effective new therapies with minimal side effects.

This invention identifies for the first time a new receptor protein, its amino acid sequence, and its human gene. Furthermore, this invention describes a previously unrecognized group of receptors within the definition of a 5-HT$_{1E}$ receptor. The information and experimental tools provided by this discovery are useful to generate new therapeutic agents, and new therapeutic or diagnostic assays for this new receptor protein, its associated mRNA molecule or its associated genomic DNA. The information and experimental tools provided by this discovery will be useful to generate new therapeutic agents, and new therapeutic or diagnostic assays for this new receptor protein, its associated mRNA molecule, or its associated genomic DNA.

Specifically, this invention relates to the first isolation of a human cDNA and genomic clone encoding a 5-HT$_{1E}$ receptor. A new human gene for the receptor identified herein as 5-HT$_{1E}$ has been identified and characterized, and a series of related cDNA and genomic clones have been isolated. In addition, the human 5-HT$_{1E}$ receptor has been expressed in Ltk$^-$ cells and Y1 cells by transfecting the cells with the plasmid pcEXV-hp75d. The pharmacological binding properties of the protein encoded have been determined, and these binding properties classify this protein as a serotonin 5-HT$_{1E}$ receptor. Mammalian cell lines expressing this human 5-HT$_{1E}$ receptor at the cell surface have been constructed, thus establishing the first well-defined, cultured cell lines with which to study this 5-HT$_{1E}$ receptor.

The invention will be better understood by reference to the Experimental Details which follow, but those skilled in the art will readily appreciate that the specific experiments detailed are only illustrative of the invention as described more fully in the claims which follow thereafter.

MATERIALS and METHODS

Cloning and Sequencing

A human placental genomic library (Stratagene) was screened using oligonucleotides derived from the human 5-HT$_{1D\beta}$ receptor gene (U.S. Ser. No. 520,716), as a probe. Overlapping oligomers complementary to the 5-HT$_{1D\beta}$ sequence in transmembrane domains III, V and VI were labeled with $^{32}$P-dATP and $^{32}$P-dCTP by synthesis with the large fragment of DNA Polymerase (Maniatis et al., 1982). Hybridization was performed at 40° C. in a solution containing 25% formamide, 10% dextran sulfate, 5× SSC (1× SSC is 0.15M sodium chloride, 0.015M sodium citrate), 1× Denhardt's (0.02% polyvinylpyrrolidone, 0.02% Ficoll, and 0.02% bovine serum albumin), and 200 µg/ml of sonicated salmon sperm DNA. The filters were washed at 40° C. in 0.1× SSC containing 0.1% sodium dodecyl sulfate (SDS) and exposed at −70° C. to Kodak XAR film in the presence of an intensifying screen. Lambda phage hybridizing to the probe were plaque purified and DNA was prepared for Southern blot analysis (Southern, 1975; Maniatis et al., 1982). For subcloning and further Southern blot analysis DNA was inserted into pUC18 (Pharmacia, Piscataway, N.J.). Nucleotide sequence analysis was done by the Sanger dideoxy nucleotide chain-termination method (Sanger 1977) on denatured double-stranded plasmid templates using Sequenase (U.S. Biochemical Corp., Cleveland, Ohio).

Expression

The entire coding region of clone hp75d was cloned into the eukaryotic expression vector pcEXV-3 (Miller, 1986). Stable cell lines were obtained by cotransfection with the plasmid pcEXV-3 (containing the 5-HT$_{1E}$ receptor gene) and the plasmid pGCcos3neo (containing the aminoglycoside transferase gene) into Ltk$^-$ cells and Y1 cells using calcium phosphate (reagents obtained from Specialty Media, Lavellette, N.J.). The cells were grown in a controlled environment (37° C., 5% CO$_2$) as monolayers in Dulbecco's modified Eagle medium (Gibco, Grand Island, N.Y.) or Flo Medium Specialty Media, Inc., Lavallette, N.J.) containing 25 mM glucose and supplemented with 10% bovine calf serum, 100 U/ml penicillin G and 100 µg/ml streptomycin sulfate. Stable clones were then selected for resistance to the antibiotic G-418 and harvested membranes were screened for their ability to bind [$^3$H] serotonin.

Detection of 5-HT$_{1E}$ Receptor mRNA in Brain Using PCR

Total RNA from human brain tissue was extracted using the RNasol protocol as described by the manufacturer. cDNA was prepared from 5 µg of total RNA with random hexanucleotide primers (500 pmoles) using Superscript reverse transcriptase (BRL, MD.) in 50 mM Tris-HCL pH 8.3 buffer containing 40 u RNasin, 2.5 mM MgCl$_2$, 50 mM KCL and 1 mM dNTPs, at 42° C. for 1 hr. The reaction was stopped by heating at 95° C. for 5 min. and chilled on ice. After terminating the reaction, RNase H (2 u) was added and incubated at 37° C. for 20 min. An aliquot (1 µg) of the first strand cDNA was diluted (1:5) into a 50 µl PCR reaction mixture (200 µM dNTPs final concentration) containing 1.25 U of Taq polymerase (Cetus Corp., Calif.) in the buffer supplied by the manufacturer, and 1 µM of 5' primer=5' TACCACGCGGCCAAGAGCCTTTACCA 3' (Seq. I.D. No. 9) and 3' primer=5'TGGTGCTAGAGATCTGCTGACGTTC 3' (Seq. I.D. No. 10), oligonucleotides derived from the third cytoplasmic loop region. The PCR amplification reaction was carried out on a Perkin Elmer Cetus thermal cycler by first a 5 min. incubation at 95° C. followed by 30 rounds of the following cycle: 2 min. at 94° C., 2 min. at 42° C., 3 min. at 72° C., with a 3" extension, followed at the end by a 15 min. incubation at 72° C. In order to control for the amplification of DNA (carried over during the RNA extraction), control PCR reactions were run in parallel with RNA diluted in the same manner as the cDNA samples. If necessary, RNA samples were pretreated with RNase-free DNase to eliminate any contaminating DNA. Positive controls were included in all experiments, consisting of plasmid containing 5HT1E receptor gene sequences. The products of the PCR amplification were separated by electrophoresis in 1.5% agarose. Amplified fragments were identified by blotting the gel to nitrocellulose and probing with an oligonucleotide internal to the 5'- and 3'-primers (5'GAGAAGTCA-GACACACAGAAAGTCTGTGTAAGTTTTACAACTTGC 3') (Seq. I.D. No. 11) and end-labeled with [c-$^{32}$P]ATP using T$_4$ polynucleotide kinase. Hybridization was performed at 40° C. in a solution containing 50% formamide, 10% dextran sulfate, 5× SSC (1× SSC is 0.15M sodium chloride, 0.015M sodium citrate), 1× Denhardt's (0.02% polyvinylpyrrolidone, 0.02% Ficoll, and 0.02% bovine serum albumin), and 200 µg/ml of sonicated salmon sperm DNA. The filters were washed at 50° C. in 0.1× SSC containing 0.1% sodium dodecyl sulfate and exposed at 70° C. to Kodak XAR film in the presence of an intensifying screen.

Membrane Preparation

Membranes were prepared from transfected Ltk$^-$ cells which were grown to 100% confluency. The cells were washed twice with phosphate-buffered saline, scraped from the culture dishes into 5 ml of ice-cold phosphate-buffered saline, and centrifuged at 200×g for 5 min at 4° C. The pellet was resuspended in 2.5 ml of ice-cold Tris buffer (20 mM Tris -HCl, pH 7.4 at 23° C., 5 mM EDTA) and homogenized by a Wheaton tissue grinder. The lysate was subsequently centrifuged at 200×g for 5 min at 4° C. to pellet large fragments which were discarded. The supernatant was collected and centrifuged at 40,000× g for 20 min at 4° C. The pellet resulting from this centrifugation was washed once in ice-cold Tris buffer and finally resuspended in a final buffer containing 50 mM Tris-HCl and 0.5 mM EDTA, pH 7.4 at 23° C. Membrane preparations were kept on ice and utilized within two hours for the radioligand binding assays. Protein concentrations were determined by the method of Bradford (1976) using bovine serum albumin as the standard.

Radioligand Binding [$^3$H]5HT binding was performed using slight modifications of the 5-HT$_{1E}$ assay conditions reported by Leonhardt et al. (1989) with the omission of masking ligands. Radioligand binding studies were achieved at 37° C. in a total volume of 250 µl of buffer (50 mM Tris, 10 mM MgCl$_2$, 0.2 mM EDTA, 10 µM pargyline, 0.1% ascorbate, pH 7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 min for both saturation and displacement studies based upon initial investigations which determined equilibrium binding conditions. Nonspecific binding was defined in the presence of 10 µM 5-HT. Binding was initiated by the addition of 50 µl membrane homogenates (10–20 µg). The reaction was terminated by rapid filtration through presoaked (0.5% polyethyleneimine) filters using 48R Cell Brandel Harvester (Gaithersburg, Md.). Subsequently, filters were washed for 5 seconds with ice cold buffer (50 mM Tris HCL, pH 7.4 at 4° C.), dried and placed into vials containing 2.5 ml of Readi-Safe (Beckman, Fullerton, Calif.) and radioactivity was measured using a Beckman LS 5000TA liquid scintillation counter. The efficiency of counting of [$^3$H]5HT averaged between 45–50%. Binding data was analyzed by computer-assisted nonlinear regression analysis (Accufit and Accucomp, Lundon Software, Chagrin Falls, Ohio). $IC_{50}$ values were converted to Ki values using the Cheng-Prusoff equation (1973). All experiments were performed in triplicate.

Measurements of cAMP Formation

Transfected Y1 cells (expression level=688 fmol/mg of protein) were incubated in DMEM, 5 mM theophylline, 10 mM Hepes (4-[2-Hydroxyethyl]-1-piperazineethanesulfonic acid), 10 µM pargyline, for 20 minutes at 37° C., 5% $CO_2$. A 5-HT dose-effect curve was then conducted by adding 12 different final concentrations of drug ranging from 10 uM to 0.1 nM, followed immediately by the addition of forskolin (10 µM). Subsequently, the cells were incubated for an additional 10 minutes at 37° C., 5% $CO_2$. The media was aspirated and the reaction terminated by the addition of 100 mM HCl. The plates were stored at 4° C. for 15 minutes and centrifuged for 5 minutes (500×g at 4° C.) to pellet cellular debris. Aliquots of the supernatant fraction were then stored at −20° C. prior to assessment of cAMP formation by radioimmunoassay (cAMP Radioimmunoassay kit, Advanced Magnetics, Cambridge, Mass.).

Detection of $5\text{-}HT_{1E}$ Receptor mRNA in Brain Using in Situ Hybridization Histochemistry Labeling of $5\text{-}HT_{1E}$ receptor oligo probe with digoxigenin-11-dUTP: The $5\text{-}HT_{1E}$ receptor oligo probe (45 mer sequence: GATGGTACACTGGCTGGGGGGTGGGCTGAGTTGACGGTGGCT) (Seq. I.D. No. 12) was synthesized in Molecular Biology Department of Neurogenetic Corp. The 3' end tailing reaction was as follows: To a sterile 1.5 ml Eppendorf tube add (1) 8 µl of $5\text{-}HT_{1E}$ receptor oligo probe (520 ng, denatured at 95° C., then chilled on ice); (2) 8 µl of 5× tailing buffer (BRL); (3) 5 µl of digoxigenin-11-dUTP (Boehringer); (4) 4 µl of dATP at 1/50 dilution; (5) 7 µl of terminal transferase (TdT, BRL); (6) 7 µl of distilled water. The above reaction mixture was incubated at 37° C. for 5 min. The tailed oligo probe was purified by ethanol precipitation, vacuum dried and reconstituted in 40 µl of distilled water.

Tissue Preparation

Guinea pig brains were dissected and frozen, first in methylbutane, then on dry ice. Brain sections were cut at 11 µm on a cryostat, thaw-mounted on gelatin-coated slides, and stored at −80° C. On the day of the experiment, the brain sections were quickly brought to room temperature using a cool air stream, and fixed in 3% paraformaldehyde made up in 0.1M PBS containing 0.02% diethylpyrocarbonate (DEPC). After rinsed in 0.1M PBS and 2× SSC, the tissue sections were dehydrated in graded ethanol and air dried.

Prehybridization

All the tissue sections were pre-incubated with hybridization buffer in a humid chamber at 25° C. for 1 hr. Twenty ml of the hybridization buffer contained (1). 10 ml of 100% formamide; (2) 4 ml of 20×SSC; (3) 0.4 ml of 50× Denhardts; (4) 1.0 ml of 10 mg/ml salmon sperm DNA; (5) 0.5 ml of 10 mg/ml yeast tRNA; (6) 4 ml of Dextran sulfate.

Hybridization

The digoxigenin labeled $5\text{-}HT_{1E}$ oligo probe (40 µl) was diluted in 1 ml of hybridization buffer. Each tissue section was then covered with 0.1 ml of the hybridization buffer with probe and incubated at 40° C. for 82 hr. After incubation all the sections were washed in 2× SSC (25° C., 1 hr), in 1× SSC (25° C., 1 hr), finally in 0.5× SSC, first 37° C. 30 min, then 25° C. 30 min.

Immunological Detection

Following the post-hybridization washes slides were rinsed in Buffer #1 (100 mM Tris-HCl; 150 mM NaCl; pH 7.5) for 1 min, then incubated with 2% normal sheep serum plus 0.3% triton X-100 in Buffer #1 for 30 min. After this preparation the sections were incubated with anti-digoxigenin conjugated with alkaline phosphatase at dilution 1:500 in Buffer #1 containing 1% normal sheep serum and 0.3% triton X-100 at RT for 1.5 hr, then at 4° C. overnight. The next day the tissue sections were rinsed in Buffer #1 for 10 min, then in Buffer #2 (100 mM Tris-HCl; 100 mM NaCl; 50 mM $MgCl_2$; pH 9.5) for 10 min. The chromagen solution was prepared immediately before the colorimetric reaction: i.e. to 10 ml of Buffer #2, (1) 45 µl of 4-nitro blue tetrazolium chloride (NBT, 75 mg/ml in 70% dimethylformamide); (2) 35 µl of 5-bromo-4-chloro-3-indolyl-phosphate (x-phosphate, 50 mg/ml in 100% dimethylformamide); and (3) 2.5 mg of levamisole were added. In order to carry out the colorimetric reaction sections were incubated with the chromogen solution in a humid, light-tight box overnight. The chromogen reaction was halted by rinsing the slides in Buffer #3 (10 mM Tris-HCl; 1 mM EDTA; pH 8.0). The sections were then rinsed in PBS, covered with Aquamount, and examined under a light microscope.

Drugs

[$^3$H]5-HT (specific activity=28 Ci/mmole) was obtained from New England Nuclear, Boston, Mass. All other chemicals were obtained from commercial sources and were of the highest grade purity available.

RESULTS

Isolation of a Genomic Clone Encoding a $5HT_{1E}$ Receptor

A human genomic placental library was screened with oligonucleotide probes derived from transmembrane domains III, V and VI of the $5\text{-}HT_{1D\beta}$ receptor gene. The hybridization of these probes with the library was performed at low stringency and the result was the appearance of several hundred positive signals. Subsequently, approximately 350 of these clones were purified and categorized into various groups, based upon which of the three probes were responsible for the hybridization signal associated with a given clone. One group of clones exhibited hybridization signals with both transmembrane domain probes III and V. A number of these clones were subject to Southern blot analysis and determined to be identical or overlapping clones. A representative of this group, hp75d, was further characterized by nucleic acid sequence analysis and encoded what appeared to be a new serotonin receptor based upon its deduced amino acid sequence.

Nucleotide Sequence and Deduced Amino Acid Sequence of hp75d

DNA sequence information obtained from clone hp75d is shown in FIG. 1. An open reading frame extending from an ATG start codon at position 1 to a stop codon at position 1095 can encode a protein 365 amino acids in length, having a relative molecular mass ($M_r$) of 41,633. A comparison of this protein sequence with previously characterized neurotransmitter receptors indicates that hp75d encodes a receptor which is a new member of a family of molecules which span the lipid bilayer seven times and couple to guanine nucleotide regulatory proteins (the G protein-coupled receptor family). A variety of structural features which are invariant in this family were present including the aspartic acid residues of transmembrane regions II and III, the DRY sequence at the end of transmembrane region III, and the conserved proline residues of transmembrane regions IV, V, VI and VII (Hartig et al. and references therein), were present in clone hp75d. A comparison of the transmembrane homology of hp75d to the other cloned serotonin receptors is shown in FIG. 2 and exhibits the following order of identity: $5\text{-HT}_{1D\beta}$ (65%), $5\text{-HT}_{1D\beta}$ (64%), $5\text{-HT}_{1A}$ (52%), $5\text{-HT}_{1C}$ (40%) and $5\text{-HT}_2$ (39%).

Receptor Expression in Transfected Mammalian Cells

Saturation analysis of membranes prepared from stably transfected Ltk⁻ cells demonstrated that the receptor expressed was saturable and of high affinity. Scatchard plot analysis by non-linear regression revealed a Kd of 10.3±1.2 nM (mean±S.E.M., n=7) and a Bmax consistent with a high level of expression, 10.9±2.6 picomoles/mg of protein (mean±S.E.M., n=7). The percent specific binding determined at the measured Kd value for [$^3$H]5-HT was greater than 85% of total binding. Furthermore, evidence that the receptor is coupled to a G-protein was demonstrated by the ability of Gpp(NH)p, a non-hydrolyzable analog of GTP, to inhibit the specific binding of [$^3$H]5-HT ($IC_{50}$=1885±556, $n_H$=0.87±0.04, $I_{max}$=26.4±5.6%).

Pharmacological analysis of the receptor was accomplished by testing the ability of drugs from different chemical classes to displace [$^3$H]5-HT specific binding (Table 1). Of the compounds investigated, 5-HT and 5-hydroxylated tryptamine derivatives possessed the highest affinity which according to the classification system of Peroutka

| COMPOUND | Ki (nm) |
| --- | --- |
| 5-HT | 10.9 ± 1.0 |
| Lysergol | 42.8 ± 5.3 |
| Ergonovine | 87.7 ± 7.6 |
| Methylergonovine | 89.4 ± 4.2 |
| a-Methyl-5-HT | 121 ± 13 |
| Methiothepin | 194 ± 4 |
| 1-Napthylpiperazine | 207 ± 69 |
| Methysergide | 228 ± 16 |
| Oxymetazoline | 419 ± 49 |
| 5-Methoxy-N,N-DMT | 528 ± 32 |
| Ergotamine | 599 ± 39 |
| 2-Methyl-5-HT | 817 ± 203 |
| Yohimbine | 1270 ± 233 |
| Sumatriptan | 2520 ± 135 |
| Tryptamine | 2559 ± 827 |
| DOI | 2970 ± 592 |
| 5-Methoxytryptamine | 3151 ± 1041 |
| 8-OH-DPAT | 3333 ± 310 |
| Rauwolscine | 3434 ± 102 |
| Spiperone | 5051 ± 689 |
| TFMPP | 6293 ± 259 |
| 5-CT | 7875 ± 284 |
| Ketanserin | >10,000 |
| Pindolol | >10,000 |
| Zacopride | >10,000 |
| LY-165163 (PAPP) | >10,000 |
| DP-5-CT | >10,000 | and Snyder (1979) makes this site a member of the $5\text{-HT}_1$ class. Interestingly, 5-CT possessed low affinity and, thus, discriminates this receptor from that of the $5\text{-HT}_{1D}$ receptor as well as other members of this class. Various ergoline compounds also bound with high affinity including agents which have potent hallucinogenic activity. Excluding methiothepin and 1-napthylpiperazine (Ki values=194 and 207 nM, respectively), piperazine derivatives had low affinity and displayed Ki values greater than 700 nM. Furthermore, rauwolfia alkaloids and serotonergic agents that possess high affinity for various subtypes of receptor within the serotonin family including ketanserin ($5\text{-HT}_2$), 8-OH-DPAT ($5\text{-HT}_{1A}$), DOI ($5\text{-HT}_{1C}$/$5\text{-HT}_2$), spiperone ($5\text{-HT}_{1A}$/$5\text{-HT}_2$), pindolol ($5\text{-HT}_{1A}$/$5\text{-HT}_{1B}$) and zacopride ($5\text{-HT}_3$) had very poor affinity. In all cases, the Hill Coefficients did not differ significantly from unity. Taken together, the pharmacological profile of the $5\text{-HT}_{1E}$ receptor is unique and contrasts to that of other known serotonin receptors. Accordingly, the probability of developing selective drugs for this receptor subtype is increased. Additional supporting evidence that the $5\text{-HT}_{1E}$ receptor is functionally coupled to a G-protein was obtained by testing the ability of 5-HT to inhibit forskolin-stimulated cAMP production in Y1 cells transfected with the $5\text{-HT}_{1E}$ receptor. FIG. 4 demonstrates that the endogenous indoleamine, 5-HT, produced a concentration-related decrease in forskolin-stimulated cAMP production with an $EC_{50}$ of 23.1 nM. The maximum inhibition of cAMP production was 32%.

The tissue distribution of $5HT_{1E}$ receptor mRNA was detected using PCR technology on cDNA from tissue-derived total RNA. The mRNA localization in human brain tissues demonstrates the presence of $5HT_{1E}$ in: frontal cortex, cerebellar cortex, temporal cortex, choroid plexus, hippocampus, brain stem and cortex. We have not identified an area of the brain which does not contain $5HT_{1E}$. We conclude that the $5HT_{1E}$ mRNA is abundant in human brain. These findings suggest that the $5HT_{1E}$ receptor is not restricted to any one region of the brain and possibly cell type, but is expressed in numerous neuronal cell groups in many distinct regions of the human brain, as has been described for $5HT_{1C}$.

The presence of $5HT_{1E}$ receptor mRNA in various regions of the human brain suggest that $5HT_{1E}$ may modulate a number of the central actions attributed to serotonin. The abundance of $5HT_{1E}$ receptors (mRNA) in the hippocampus may affect mood, behavior and hallucinogenesis. A greater understanding of possible physiological roles of this receptor subtype may be realized by the development of more specific $5HT_{1E}$ receptor drugs as well as physiological manipulations of $5HT_{1E}$ mRNAs/receptors.

The cellular localization of $5\text{-HT}_{1E}$ receptor mRNA was detected with digoxigenin-11-dUTP labeled oligo probes employing in situ hybridization(ISHH) technology. Digoxigenin-11-dUTP labeled oxytocin(OT) oligo probes were used as a positive control for the experiment since the distribution of OT neurons in the central nervous system is well known. OT cells were intensely stained in the Guinea Pig's hypothalamus. Tissue sections pre-treated with RNase A were used as a negative control. Guinea pig brain sections were examined under a light microscope. $5\text{-HT}_{1E}$ receptor mRNA was found in cells located in the frontal cortex, piriform cortex, hippocampus (CA1, CA2 and CA3), lateral septal nucleus, triangular septal nucleus, septofimbrial nucleus and the basal ganglia (caudate-putamen and globus pallidus). It was detected in the amygdaloid complex, the bed nucleus stria terminalis and the hypothalamic area including anterior hypothalamus, periventricular nucleus, paraventricular nucleus (magnocellular and parvocellular populations), supraoptic nucleus which seemed to include both vasopressin and oxytocin cell populations, and the lateral hypothalamus. The 1E receptor mRNA was also detected in the thalamic area including anteroventral thalamic, anterodorsal thalamic, mediodorsal thalamic, ventrolateral thalamic, reticular thalamic paracentral thalamic, paratenial thalamic nuclei and the nucleus stria medullaris. Control sections pre-treated with RNase A did not exhibit any staining pattern.

Experimental Discussion

The deduced amino acid sequence of hp75d was analyzed to uncover relationships between it and the other cloned serotonin receptor sequences. Although the homology within the membrane spanning domains was greatest with the 5-HT$_{1D\beta}$ receptor (FIG. 2), the nature of this newly cloned receptor could not be clearly predicted. The rational for this ambiguity is the interpretation of the transmembrane domain homology (approximately 65%) to the 5-HT$_{1D\beta}$ and 5-HT$_{1D\beta}$ receptor subfamily. Closely related members of a "subfamily" of serotonin receptors (i.e. "subtypes") generally share a common transmitter and also have similar pharmacological profiles and physiological roles (for example, 5-HT$_2$ and 5-HT$_{1C}$ or 5-HT$_{1D\alpha}$ and 5-HT$_{1D\beta}$). Such "subtypes" display an amino acid identity of approximately 75–80% in their transmembrane domains. Serotonin receptors which are not members of the same "subfamily", but are members of the serotonin "family" (in which the receptors use the same neurotransmitter; i.e. 5-HT$_2$ and 5-HT$_{1D\alpha}$) generally show much lower transmembrane homology (approximately 45%). Such transmembrane amino acid homologies can, therefore, give insight into the relationship between receptors and be used as predictors of receptor pharmacology. According to this type of analysis, although the newly cloned receptor appears to be more related to the 5-HT$_{1D}$ subfamily, it is likely to be in a subfamily distinct from all the other serotonin receptors.

The present pharmacological evidence substantiates the existence of a novel serotonin receptor in the human brain as first suggested by Leonhardt et al. (1989). Comparison of the pharmacological profile observed in native cortical membranes to that revealed for the cloned 5-HT$_{1E}$ receptor yielded a correlation coefficient of 0.987 (FIG. 3). Indeed, there were some differences in measured affinity constants but the relative values of selected drugs performed in both studies was similar. In this regard, a close examination of the Scatchard plot analysis performed in the study by Leonhardt et al. (1989) reveals that the reported Kd value may have been underestimated since the radioligand concentrations did not exceed 10 nM. In order to have accurately determined the dissociation constant, the radioligand concentration should have been extended to at least 50 nM or 10 times the estimated Kd (Yamamura et al., 1985). The initial study, however, was limited in tissue supply and lacked a comprehensive pharmacological characterization. The cloning of the 5-HT$_{1E}$ site will now allow more extensive investigations into the nature of this unique receptor.

The structure-activity relationships observed in the present study suggest that there are important requirements for high affinity binding to the 5-HT$_{1E}$ receptor. Substitution or removal of the 5-hydroxy group on serotonin decreases the affinity 300 fold for the receptor (egs., tryptamine, 5-methoxytryptamine and 5-carboxyamidotryptamine). Additionally, 2-methylation and α-methylation of 5-HT essentially abolishes its affinity for the 5-HT$_{1E}$ site. In contrast to these substitutions, N,N -dimethylation of the aliphatic side chain of the indole ring increases the affinity approximately 20 fold (unpublished observations). Basic structural requirements of the ergoline derivatives demonstrate that N-methylation of the indole ring decreases affinity as does bulky substitutions. Furthermore, piperazine derivatives are not bound at high affinity.

Notably, the application of the human 5-HT$_{1E}$ receptor clone to pharmaceutical research can lead to new drug design and development. The localization of this receptor in the cerebral cortex (Leonhardt et al., 1989) and parts of the basal ganglia such as the putamen and globus pallidus (Lowther et al., 1991) suggests a putative link to limbic, cognitive and/or motor function (Nieuwenhuys et al., 1988; Kandel and Schwartz, 1985) and, thus, may be involved in such abnormal conditions as dementia, Parkinson's disease, feeding disorders, anxiety and schizophrenia. Notably, the ergot compounds that possess affinity for this site have been demonstrated to affect these type of behaviors in humans as well as animals (Wilkinson and Dourish, 1991). In relation to this, it appears that the 5-HT$_{1E}$ binding site is also present in rat and bovine brain (Leonhardt et al., 1989) as well as guinea-pig, rabbit and dog where the data was initially interpreted as evidence for subtypes of the 5-HT$_{1D}$ receptor (Middlemiss, 1990). Nonetheless, it must be taken into consideration that this novel site can possibly lead to selective drug therapy devoid of side effects. In regard to this, serotonin uptake blockers are effective in treating neuropsychiatric disorders such as depression and obsessive-compulsive illness (Blier et al., 1987; Asberg et al., 1986; Insel et al., 1985). However, these agents have side effects and, in fact, the mechanism of action for these compounds are not linked to any particular serotonergic receptor. The possibility that agents selective for the 5-HT$_{1E}$ receptor may have clinical utility as antidepressants, for example, without the side effects attributed to current treatment modalities can have significant implications for drug therapy. Furthermore, it should be noted that ergoline derivatives have had clinical usefulness as drugs capable of relieving migraines and, thus, the involvement of the 5-HT$_{1E}$ receptor in this disorder deserves future attention. Ultimately, in depth investigations into the localization of the 5-HT$_{1E}$ receptor in brain and peripheral tissue will target new sites that can lead to specific functional roles for this serotonergic receptor.

Another consideration for therapeutic application of this site may be related to the treatment of feeding disorders such as obesity, bulimia nervosa and/or anorexia nervosa. The involvement of serotonin and feeding behavior has received much attention during the last decade. It is now known that many of the identified and well-characterized serotonergic receptors are capable of modulating feeding (Blundell and Lawton, 1990). Notably, serotonin uptake blockers which have been used to treat feeding disorders act nonselectively and as such have side-effect potential (Jimerson et al., 1990). Although many different serotonergic receptors are involved in feeding, the search for the one site that can be exploited for selective drug development has yet to be found. There is no doubt that interest exists in finding drugs that interact with the serotonin system for the treatment of feeding disorders (Cooper, 1989).

Thus, the pharmacological profile of the cloned human 5-HT$_{1E}$ receptor is unique and contrasts to other known serotonergic receptors. The utility of this site expressed in a cellular system and, thus, isolated for study will create excellent opportunities in drug development directed towards a novel serotonergic receptor that may have wide-range implications for drug therapy. Indeed, the potential therapeutic applications may extend to neuropsychiatric disorders including depression, anxiety, schizophrenia, dementia and obsessive-compulsive illness as well as obesity and migraine. The localization of 5-HT$_{1E}$ receptor mRNA by in situ hybridization makes it possible to predict its physiological and pathological functions. 5-HT$_{1E}$ receptor mRNA is detected in the limbic structures, such as the hippocampus, septal nuclei, piriform cortex (olfactory system), amygdaloid complex and the bed nucleus stria terminalis. The olfactory system sends afferent fibers to the hippocampus through the subiculum, and to the amygdaloid complex (Kupfermann,1985). In turn the outputs of the hippocampus project to the septal area and hypothalamus while the amygdaloid complex projects to the hypothalamus via the stria terminalis (Kupfermann, 1985). The involvement of the limbic system in emotional behavior (e.g., fear, pleasure, sexual activities) and memory is well known (Kupfermann, 1985). Therefore, the finding of $5\text{-HT}_{1E}$ receptor mRNA in these structures indicates a potential role in neuropsychiatric disorders such as depression, obsessive-compulsive illness, anxiety, schizophrenia and dementia.

The hypothalamus regulates the body adjustments to the external and internal environments. It can control hunger (the ventromedial nucleus and the lateral hypothalamus), endocrine functions (e.g. the supraoptic nucleus, the paraventricular nucleus and the periventricular nucleus), affective (emotional) behavior (the ventromedial and dorsomedial nuclei) and the activity of the visceral nervous system (the anterior hypothalamus) (Diamond et al., 1985). The discovery of $5\text{-HT}_{1E}$ receptor mRNA in these nuclei indicates physiological and pathological roles of this receptor subtype in cardiovascular, gastrointestinal, endocrine, neurological and psychiatric systems.

The thalamus is a relay station where the sensory and motor-related pathways passing up the brain stem synapse before proceeding on to the cerebral cortex for more elaborate integration and analysis. The $5\text{-HT}_{1E}$ receptor mRNA was found in the anterior thalamic nucleus which receives the input from the mammillothalamic tract and sends fibers to the cingulate gyrus. Thus, this nucleus is an important part of the circuit connecting the hypothalamus, the thalamus, and the limbic lobe (Diamond et al., 1985). The $5\text{-HT}_{1E}$ receptor mRNA was also found in the mediodorsal thalamic nucleus which is involved in emotional behavior and in the ventral lateral thalamic nucleus which connects the basal ganglia and premotor area. Furthermore, $5\text{-HT}_{1E}$ receptor mRNA was found in the nucleus reticularis thalami through which pass most of the thalamocortical and corticothalamic fibers. The axons of corticothalamic and thalamocortical neurons provide collaterals for synapse with reticular cells, exerting a facilitatory effect, while the axons of the GABA-rich reticularis cells project back on the specific thalamic neurons, continuously modulating (by inhibition) the ascending flow of thalamocortical impulses (Diamond et al., 1985). The reticularis neurons play a significant role in the interactions between the thalamus and the frontal cortex. In addition, the $5\text{-HT}_{1E}$ receptor mRNA was also visualized in the basal ganglia including the caudate-putamen and globus pallidus both of which control motor activity (Alheid et al., 1990). These findings indicate important roles of the $5\text{-HT}_{1E}$ receptors in emotional behavior, sensation (e.g., pain) and motor activity.

REFERENCES

Alheid, G. F.; Heimer, L. & Switzer III, R. C., In: The Human Nervous System. Ed. George Paxinos, Academic Press, Inc., 1990.

Asberg, M., Eriksson, B., Matensson, B., Traskman-Bendz, L. and Wagner, A.: Therapeutic effects of serotonin uptake inhibitors in depression. J. Clin. Psychiat. 47:23–35, 1986.

Blier, P., DeMontigny, C. and Chaput, Y.: Modifications of the serotonin system by antidepressant treatments: Implications for the therapeutic response in major depression. J. Clin. Psychpharmacol. 7(6):24s–35s, 1987.

Blundell, J. E. and Lawton, C. L.: Serotonin receptor subtypes and the organization of feeding behaviour: Experimental models. In: Serotonin: From cell biology to pharmacology and therapeutics. (eds. Paoletti, R., Vanhoutte, P. M., Brunello, N. and Maggi, F. M.) Boston: Kluwer Academic Publishers, pp. 213–219, 1990.

Bradford, M.: A rapid and sensitive method for the quantification of microgram quantities of protein utilizing the principle of protein-dye binding. Anal. Biochem. 72:248–254, 1976.

Branchek, T., Weinshank, R. L., Macchi, M. J., Zgombick, J. M. and Hartig, P. R.: Cloning and expression of a human 5-HT1D receptor. The Second IUPHAR Satellite Meeting on Serotonin, Basel, Switzerland, Jul. 11–13, 1990, Abstract #2.

Cheng, Y. C. and Prusoff, W. H.: Relationship between the inhibition constant (Ki) and the concentration of inhibitor which causes 50% inhibition (IC50) of an enzyme reaction. Biochem. Pharmacol. 22:3099–3108, 1973.

Cooper, S. J.: Drugs interacting with 5-HT systems show promise for treatment of eating disorders. TIPS 10:56–57, 1989.

Diamond, M. C.; Scheibel, A. B. and Elson, L. M.: The human brain coloring book. Barnes & Noble Books, 1985

Fargin, A., Raymond, J. R., Lohse, M. J., Kobilka, B. K. Caron, M. G. and Lefkowitz, R. J.: The genomic clone G-21 which resembles a β-adrenergic receptor sequence encodes the 5-HT1A receptor. Nature 335:358–360, 1988.

Gaddum, J. H. and Picarelli, Z. P.: Two kinds of tryptamine receptor. Brit. J. Pharmacol. 12:323–328, 1957.

Glennon, R. A.: Serotonin receptors: Clinical implications. Neurosci. Biobehav. Rev. 14:35-47, 1990.

Green, A. R.: Neuropharmacology of serotonin. Oxford: Oxford University Press, 1985.

Hamon, M., Lanfumey, L., El Mestikawy, S., Boni, C., Miquel, M.-C., Bolanos, F., Schechter, L. and Gozlan, H.: The main features of central 5-HT1 receptors. Neuropsychopharmacol. 3(5/6):349–360, 1990.

Hartig, P. R., Kao, H.-T., Macchi, M., Adham, N., Zgombick, J., Weinshank, R. and Branchek, T.: The molecular biology of serotonin receptors: An overview. Neuropsychopharmacol. 3(5/6):335–347, 1990.

Insel, T. R., Mueller, E. A., Alterman, I., Linnoila, M. and Murphy, D. L.: Obsessive-compulsive disorder and serotonin: Is there a connection? Biol. Psychiat. 20:1174–1188, 1985.

Jimerson, D. C., Lesem, M. D., Hegg, A. P. and Brewerton, T. D.: Serotonin in human eating disorders. Ann. N.Y. Acad. Sci. 600:532–544, 1990.

Julius, D., MacDermott, A. B., Axel, R. and Jessell, T. M.: Molecular characterization of a functional cDNA encoding the serotonin 1C receptor. Science 241:558–564, 1988.

Kandel, E. R. and Schwartz, J. H.: Principles of neuroscience. New York: Elsevier Publishing Co., 1985.

Kupfermann, I.: Hypothalamus and limbic system. In: Principles of neuroscience. Eds: Kandel, E. R. and Schwartz, J. H., New York: Elsevier Publishing Co.,1985

Leonhardt, S., Herrick-Davis, K. and Titeler, M.: Detection of a novel serotonin receptor subtype (5-HT1E) in human brain: Interaction with a GTP-binding protein. J. Neurochem. 53(2):465–471, 1989.

Lowther, S., De Paermentier, F., Crompton, M. R., Katona, C. L. E. and Horton, R. W.: $5\text{HT}_{1D}$ and $5\text{HT}_{1E}$ binding sites in depression: A post-mortem study in suicide victims. Serotonin 1991- 5-Hydroxytryptamine—CNS Receptors and Brain Function, Birmingham, UK, Jul. 14–17, 1991, p. 175, Abstract #P. 145.

Maniatis, T., Fritsch, E. F., and Sambrook, J. Molecular Cloning: A Laboratory Manual, Cold Spring Harbor Laboratory, Cold Spring Harbor, N.Y., 1982.

Middlemiss, D. N., Suman-Chauhan, N., Smith, S. M., Picton, C., Shaw, D. and Bevan, Y.: Subpopulations of 5-HT1D recognition sites in guinea-pig, rabbit, dog and human cortex. The Second IUPHAR Satellite Meeting on Serotonin, Basel, Switzerland, Jul. 11–13, 1990, Abstract #P-30.

Miller, J., and R. N. Germain. Efficient cell surface expression of class II MHC molecules in the absence of associated invariant chain. J.Exp.Med. 164:1478–1489, 1986.

Nieuwenhuys, R., Voogd, J. and van Huijzen, C.: The human nervous system: A synopsis and atlas. New York: Springer Verlag, 1988.

Osborne, N. N. and Hamon, M.: Neuronal serotonin. Chichester: John Wiley and Sons, Inc., 1988.

Peroutka, S. J.: Serotonin receptor subtypes: Basic and clinical aspects. New York: Wiley-Liss, Inc., 1991.

Peroutka, S. J. and Snyder, S. H.: Multiple serotonin receptors, differential binding of [$^3$H]5-hydroxytryptamine, [$^3$H]lysergic acid diethylamide and [$^3$H]spiroperidol. Mol. Pharmacol. 16:687–699, 1979.

Pritchett, D. B., Bach, A. W. J., Wozny, M., Taleb, O., Dal Toso, R., Shih, J. and Seeburg, P. H.: Structure and functional expression of cloned rat serotonin 5-HT2 receptor. EMBO J. 7:4135–4140, 1988.

Rapport, M. M., Green, A. A. and Page, I. H.: Purification of the substance which is responsible for vasoconstrictor activity of serum. Fed. Proc. 6:184, 1947.

Rapport, M. M.: Serum vasoconstrictor (serotonin) V. Presence of creatinine in the complex. A proposed structure of the vasoconstrictor principle. J. Biol. Chem. 180:961–969, 1949.

Sanger, S. DNA sequencing with chain-terminating inhibitors. Proc. Natl.Acad. Sci.USA 74:5463–5467, 1977.

Sanders-Bush, E.: The Serotonin Receptors. Clifton, N.J.: Humana Press, 1988.

Southern, E. M. Detection of specific sequences among DNA fragments separated by gel electrophoresis. J.Mol.Biol. 98:503–505, 1975.

Wilkinson, L. O. and Dourish, C. T.: Serotonin and animal behavior. In: Serotonin receptor subtypes: Basic and clinical aspects. (ed. Peroutka, S. J.) New York:Wiley-Liss, Inc., pgs. 147–210, 1991.

Yamamura, H. I., Enna, S. J. and Kuhar, M. J.: Neurotransmitter receptor binding. New York: Raven Press, 1985.

---

What is claimed is:

1. An isolated nucleic acid molecule encoding a human 5-$HT_{1E}$ receptor, having the amino acid sequence shown in FIG. 1.

2. An isolated nucleic acid molecule of claim 1, wherein the nucleic acid molecule is a DNA molecule.

3. An isolated nucleic acid molecule of claim 2, wherein the DNA molecule is a cDNA molecule.

4. A vector comprising the nucleic acid molecule of claim 1.

5. A vector of claim 4 adapted for expression in a mammalian cell which comprises the regulatory elements necessary for expression of the nucleic acid in the mammalian cell so located relative to the nucleic acid encoding the 5-$HT_{1E}$ receptor as to permit expression thereof.

6. A plasmid comprising the vector of claim 5.

7. A mammalian cell comprising the plasmid of claim 6.

8. A plasmid comprising the vector of claim 4.

9. A thymidine kinase deficient L(Ltk⁻) cell comprising the plasmid of claim 8.

10. A Y1 cell comprising the plasmid of claim 8.

11. A plasmid which is pcEXV-hp75d (ATCC Accession No. 75138).

12. An Ltk⁻ cell comprising the plasmid of claim 11 which is 5-$HT_{1E}$-7 (ATCC Accession No. CRL 10913).

13. A Y1 cell comprising the plasmid of claim 11 which is Y-5-$HT_{1E}$ (ATCC Accession No. CRL 10914).

* * * * *